United States Patent
Büttner et al.

(10) Patent No.: US 9,976,135 B2
(45) Date of Patent: May 22, 2018

(54) HUMAN TRYPSINOGEN WITH REDUCED AUTOACTIVATION AND ITS USE IN AN IMMUNOASSAY

(71) Applicant: Life Science Inkubator GmbH, Bonn (DE)

(72) Inventors: Karin Büttner, Leipzig (DE); Agneta Prasse, Leipzig (DE); Thole Zuchner, Schriesheim (DE)

(73) Assignee: LIFE SCIENCE INKUBATOR GMBH, Bonn (DE)

( * ) Notice: Subject to any disclaimer, the term of this patent is extended or adjusted under 35 U.S.C. 154(b) by 3 days.

(21) Appl. No.: 15/026,604

(22) PCT Filed: Sep. 25, 2014

(86) PCT No.: PCT/EP2014/070549
§ 371 (c)(1),
(2) Date: Apr. 1, 2016

(87) PCT Pub. No.: WO2015/049166
PCT Pub. Date: Apr. 9, 2015

(65) Prior Publication Data
US 2016/0237419 A1    Aug. 18, 2016

(30) Foreign Application Priority Data
Oct. 2, 2013 (EP) .................................. 13187194

(51) Int. Cl.
*C12Q 1/37* (2006.01)
*C12N 9/76* (2006.01)
*G01N 33/542* (2006.01)

(52) U.S. Cl.
CPC ............. *C12N 9/6427* (2013.01); *C12Q 1/37* (2013.01); *G01N 33/542* (2013.01); *C12Y 304/21004* (2013.01)

(58) Field of Classification Search
None
See application file for complete search history.

(56) References Cited

FOREIGN PATENT DOCUMENTS

EP    2 045 321 A2    3/2009

OTHER PUBLICATIONS

Database UniProt [Online] Apr. 1, 1988 (Apr. 1, 1988),RecName::Full=Trypsin-1; EC=3.4.21.4; AltName: Full=Beta-trypsin, AltName: Full=Cationic trypsinogen; AitName: Full=Serine protease 1; AltName:Full=Trypsin I;,XP002720473,retrieved from EBI accession No. UNIPROT:P07477 Database accession No. P07477 Version Sep. 18, 2013; sequence (available at ncbi.nlm.nih.gov/protein).
Mitsuru E et al: "Cloning, characterization and nucleotide sequences of two cDNAs encoding human pancreatic trypsinogens", GENE, vol. 41, No. 2-3, Jan. 1, 1986 (Jan. 1, 1986), pp. 305-310.
P. Simon: "Hereditary Pancreatitis Caused by a Novel PRSS1 Mutation(Arg-122 right-arrow Cys) That Alters Autoactivation and Autodegradation of Cationic Trypsinogen", Journal of Biological Chemistry, vol. 277, No. 7, Feb. 8, 2002 (Feb. 8, 2002), pp. 5404-5410.
Database Protein [Online] Oct. 25, 2012 (Oct. 25, 2012), "trypsin-1-like isoform 1 [Pongo abelii]", XP002720474, retrieved from NCBI Database (ncbi.nlm.nih.gov/protein) accession No. XP001160583.
Database Protein [Online] Jul. 17, 2012 (Jul. 17, 2012),"trypsin-1-like isoform 1 [Pongo abelii]", XP002720475, retrieved from NCBI Database (ncbi.nlm.nih.gov/protein) accession No. XP002818617.
Database Protein [Online]Aug. 25, 2012 (Aug. 25, 2012), "trypsin-1 precursor [Macaca mulatta]", XP002720476, retrieved from NCBI Database (ncbi.nlm.nih.gov/protein) accession No. NP 001040586.
Teich et al: "Hereditary chronic pancreatitis", Best Practice and Research, Clinical Gastroenterology., vol. 22, No. 1, Jan. 17, 2008 (Jan. 17, 2008), pp. 115-130.
Thomas Zauner et al: "Highly Adaptable and Sensitive Protease Assay Based on Fluorescence Resonance Energy Transfer", Analytical Chemistry, vol. 83, No. 19, Sep. 5, 2011 (Sep. 5, 2011), pp. 7356-7363 (including related supporting information).

*Primary Examiner* — Changhwa J Cheu
(74) *Attorney, Agent, or Firm* — JMB Davis Ben-David

(57) ABSTRACT

The present invention relates to a polypeptide consisting of or comprising a variant of human trypsinogen-1, comprising the substitutions: amino acid residue E64 is replaced with an amino acid residue comprising a positively charged side chain, amino acid residue K123 is replaced with an amino acid residue comprising an aliphatic side chain and amino acid residues Y139 and D147 are replaced with a glutamine or asparagine residue, and wherein said variant is further characterized in that: an amino acid residue selected from E16, E17 and E142 is replaced with an amino acid residue comprising an aliphatic side chain, and/or amino acid residue N18 is replaced with a histidine residue, and/or amino acid residue R107 is replaced with a lysine residue, and/or amino acid residue D138 is replaced with an amino acid residue comprising a positively charged side chain, and wherein said variant is cleavable into a polypeptide having a native-like enzymatic activity when compared to human trypsin-1.

14 Claims, 11 Drawing Sheets

Fig. 3

```
PRSS1-sc    1  MGFDDDDKIVGGYNCAAHSVPYQVSLNSGYHFCGGSLINEQWVVSAGHCY   50
               ||||||||||||||||| ||||||||||||||||||||||||||||||||
PRSS1-WT    1  MGFDDDDKIVGGYNCEENSVPYQVSLNSGYHFCGGSLINEQWVVSAGHCY   50

PRSS1-sc   51  KSRIQVRLGEHNIKVLEGNEQFINAAKIIRHPQYDRKTLNNDIMLIKLSS  100
               ||||||||||||| |||||||||||||||||||||||||||||||||||
PRSS1-WT   51  KSRIQVRLGEHNIEVLEGNEQFINAAKIIRHPQYDRKTLNNDIMLIKLSS  100

PRSS1-sc  101  RAVINAKVSTISLPTAPPATGTLCLISGWGNTASSGAKNPDLLQCLNAPV  150
               |||||| ||||||||||||||||||||||||||||| :  |||  |||
PRSS1-WT  101  RAVINARVSTISLPTAPPATGTKCLISGWGNTASSGADYPDELQCLDAPV  150

PRSS1-sc  151  LSQAKCEASYPGKITSNMFCVGFLEGGKDSCQGDSGGPVVCNGQLQGVVS  200
               ||||||||||||||||||||||||||||||||||||||||||||||||||
PRSS1-WT  151  LSQAKCEASYPGKITSNMFCVGFLEGGKDSCQGDSGGPVVCNGQLQGVVS  200

PRSS1-sc  201  WGDGCAQKNKPGVYTKVYNYVKWIKNTIAANS  232
               ||||||||||||||||||||||||||||||||
PRSS1-WT  201  WGDGCAQKNKPGVYTKVYNYVKWIKNTIAANS  232
```

Fig. 4

```
PRSS1-sc      1 ATGGGCTTTGATGATGATGACAAGATCGTTGGGGGCTACAACTGTGCGGC   50
                |||||||||||||||||||||||||||||||||||||||||||||||.||.
PRSS1-WT      1 ATGGGCTTTGATGATGATGACAAGATCGTTGGGGGCTACAACTGTGAGGA   50

PRSS1-sc     51 GCATTCTGTCCCCTACCAGGTGTCCCTGAATTCTGGCTACCACTTCTGTG  100
                |.||||||||||||||||||||||||||||||||||||||||||||||||
PRSS1-WT     51 GAATTCTGTCCCCTACCAGGTGTCCCTGAATTCTGGCTACCACTTCTGTG  100

PRSS1-sc    101 GTGGCTCCCTCATCAACGAACAGTGGGTGGTATCAGCAGGCCACTGCTAC  150
                ||||||||||||||||||||||||||||||||||||||||||||||||||
PRSS1-WT    101 GTGGCTCCCTCATCAACGAACAGTGGGTGGTATCAGCAGGCCACTGCTAC  150

PRSS1-sc    151 AAGTCCCGCATCCAGGTGAGACTGGGAGAGCACAACATCAAAGTCCTGGA  200
                |||||||||||||||||||||||||||||||||||||||||.||||||||
PRSS1-WT    151 AAGTCCCGCATCCAGGTGAGACTGGGAGAGCACAACATCGAAGTCCTGGA  200

PRSS1-sc    201 GGGGAATGAGCAGTTCATCAATGCAGCCAAGATCATCCGCCACCCCCAAT  250
                ||||||||||||||||||||||||||||||||||||||||||||||||||
PRSS1-WT    201 GGGGAATGAGCAGTTCATCAATGCAGCCAAGATCATCCGCCACCCCCAAT  250

PRSS1-sc    251 ACGACAGGAAGACTCTGAACAATGACATCATGTTAATCAAGCTCTCCTCA  300
                ||||||||||||||||||||||||||||||||||||||||||||||||||
PRSS1-WT    251 ACGACAGGAAGACTCTGAACAATGACATCATGTTAATCAAGCTCTCCTCA  300

PRSS1-sc    301 CGTGCAGTAATCAACGCCAAAGTGTCCACCATCTCTCTGCCCACCGCCCC  350
                |||||||||||||||||||...||||||||||||||||||||||||||||
PRSS1-WT    301 CGTGCAGTAATCAACGCCCGCGTGTCCACCATCTCTCTGCCCACCGCCCC  350

PRSS1-sc    351 TCCAGCCACTGGCACGCTGTGCCTCATCTCTGGCTGGGGCAACACTGCGA  400
                ||||||||||||||||..||||||||||||||||||||||||||||||||
PRSS1-WT    351 TCCAGCCACTGGCACGAAGTGCCTCATCTCTGGCTGGGGCAACACTGCGA  400

PRSS1-sc    401 GCTCTGGCGCCAAAAACCCAGACCTGCTGCAGTGCCTGAACGCTCCTGTG  450
                ||||||||||.|..|||||||||..|||||||||||||||.|||||||||
PRSS1-WT    401 GCTCTGGCGCCGACTACCCAGACGAGCTGCAGTGCCTGGACGCTCCTGTG  450

PRSS1-sc    451 CTGAGCCAGGCTAAGTGTGAAGCCTCCTACCCTGGAAAGATTACCAGCAA  500
                ||||||||||||||||||||||||||||||||||||||||||||||||||
PRSS1-WT    451 CTGAGCCAGGCTAAGTGTGAAGCCTCCTACCCTGGAAAGATTACCAGCAA  500

PRSS1-sc    501 CATGTTCTGTGTGGGCTTCCTTGAGGGAGGCAAGGATTCATGTCAGGGTG  550
                ||||||||||||||||||||||||||||||||||||||||||||||||||
PRSS1-WT    501 CATGTTCTGTGTGGGCTTCCTTGAGGGAGGCAAGGATTCATGTCAGGGTG  550

PRSS1-sc    551 ATTCTGGTGGCCCTGTGGTCTGCAATGGACAGCTCCAAGGAGTTGTCTCC  600
                ||||||||||||||||||||||||||||||||||||||||||||||||||
PRSS1-WT    551 ATTCTGGTGGCCCTGTGGTCTGCAATGGACAGCTCCAAGGAGTTGTCTCC  600

PRSS1-sc    601 TGGGGTGATGGCTGTGCCCAGAAGAACAAGCCTGGAGTCTACACCAAGGT  650
                ||||||||||||||||||||||||||||||||||||||||||||||||||
PRSS1-WT    601 TGGGGTGATGGCTGTGCCCAGAAGAACAAGCCTGGAGTCTACACCAAGGT  650

PRSS1-sc    651 CTACAACTATGTGAAATGGATTAAGAACACCATAGCTGCCAATAGCTAA  699
                |||||||||||||||||||||||||||||||||||||||||||||||||
PRSS1-WT    651 CTACAACTATGTGAAATGGATTAAGAACACCATAGCTGCCAATAGCTAA  699
```

HUMAN TRYPSINOGEN WITH REDUCED AUTOACTIVATION AND ITS USE IN AN IMMUNOASSAY

CROSS-REFERENCE TO RELATED APPLICATIONS

This is the U.S. National Stage of International Application No. PCT/EP2014/070549, filed Sep. 25, 2014, which was published in English under PCT Article 21(2), which in turn claims the benefit of EP Patent Application No. 13187194.9 filed Oct. 2, 2013.

Human trypsinogen (PRSS1) is the inactive precursor of the enzyme trypsin. Human enteropeptidase activates trypsinogen by cleaving off an activation peptide. However, trypsin or even trypsinogen can also cleave off this activation peptide from trypsinogen, so that trypsinogen can be activated even by minute amounts of active trypsin or by trypsinogen itself. This process is called autoactivation.

One application of trypsinogen relates to ELISA type assays, wherein enteropeptidase is covalently coupled to an antibody and activates inactive trypsinogen into active trypsin. Trypsin then cleaves a peptide bearing FRET (Förster Resonance Energy Transfer) coupled dye molecules in between the site of cleavage, leading to a change in the optical signal of the dye. The above mentioned autoactivation of trypsinogen can cause a background signal, which negatively affects the detection limit, linear range etc. Thus, a decrease of the autoactivation of trypsinogen would be desirable.

The objective of the present invention is to provide means and methods for determining or quantifying an analyte with an increased detection or quantification limit, particularly by decreasing the autoactivation of trypsinogen.

The objective is attained by the subject-matter of the independent claims of the present invention.

The present invention is based on the finding that a modification of the surface of human trypsinogen can lead to the creation of a human trypsinogen variant with a lower autoactivation. Particularly, this variant or mutant (supercharged [sc] trypsinogen) is based on modified surface charges at the site of the activation sequence. This site is far away from the substrate binding pocket to avoid any undesired effect on the substrate specificity.

Without wishing to be bound by theory the inventors believe that modification of the trypsinogen surface charge prevents a binding of another trypsinogen molecule, or a trypsin, to the trypsinogen activation site due to electrostatic repulsion between both trypsinogen and trypsin.

According to a first aspect of the invention, a polypeptide consisting of or comprising a variant of human trypsinogen-1 is provided, wherein the variant comprises the substitutions: amino acid residue E64 is replaced with an amino acid residue comprising a positively charged side chain, particularly a lysine or arginine residue; amino acid residue K123 is replaced with an amino acid residue comprising an aliphatic side chain, amino acid residues Y139 and/or D147 are replaced with a glutamine or asparagine residue, and wherein the variant is further characterized in that an amino acid residue selected from E16, E17 and E142 is replaced with an amino acid residue comprising an aliphatic side chain, and/or amino acid residue N18 is replaced with a histidine residue, and/or amino acid residue R107 is replaced with a lysine residue, and/or amino acid residue D138 is replaced with an amino acid residue comprising a positively charged side chain, particularly a lysine or arginine residue, and wherein the variant is cleavable into a polypeptide having a native-like activity when compared to human trypsin-1, which is the mature form of human trypsinogen-1 (SEQ ID NO 3).

The given positions of the amino acid replacements refer to the amino acid sequence of the human wild type trypsinogen-1 (SEQ ID NO 3).

A native-like enzymatic activity in the context of the present specification refers to an enzymatic activity that equates to at least 80%, 90% or 95% of the enzymatic activity of human wild type trypsin, particularly with similar substrate specificity when compared to human wild type trypsin.

In some embodiments, E16 and E17 are replaced each independently with an amino acid residue comprising an aliphatic side chain. In some embodiments, E16 and E142 are replaced each independently with an amino acid residue comprising an aliphatic side chain. In some embodiments, E17 and E142 are replaced each independently with an amino acid residue comprising an aliphatic side chain.

In some embodiments, E16 is replaced with an amino acid residue comprising an aliphatic side chain, and N18 is replaced with a histidine residue. In some embodiments, E16 is replaced with an amino acid residue comprising an aliphatic side chain, and R107 is replaced with a lysine residue. In some embodiments, E16 is replaced with an amino acid residue comprising an aliphatic side chain, and D138 is replaced with an amino acid residue comprising a positively charged side chain.

In some embodiments, E17 is replaced with an amino acid residue comprising an aliphatic side chain, and N18 is replaced with a histidine residue. In some embodiments, E17 is replaced with an amino acid residue comprising an aliphatic side chain, and R107 is replaced with a lysine residue. In some embodiments, E17 is replaced with an amino acid residue comprising an aliphatic side chain, and D138 is replaced with an amino acid residue comprising a positively charged side chain.

In some embodiments, E142 is replaced with an amino acid residue comprising an aliphatic side chain, and N18 is replaced with a histidine residue. In some embodiments, E142 is replaced with an amino acid residue comprising an aliphatic side chain, and R107 is replaced with a lysine residue. In some embodiments, E142 is replaced with an amino acid residue comprising an aliphatic side chain, and D138 is replaced with an amino acid residue comprising a positively charged side chain.

In some embodiments, N18 is replaced with a histidine residue, and R107 is replaced with a lysine residue. In some embodiments, N18 is replaced with a histidine residue, and D138 is replaced with an amino acid residue comprising a positively charged side chain.

In some embodiments, R107 is replaced with a lysine residue, and D138 is replaced with an amino acid residue comprising a positively charged side chain.

In some embodiments, all of E16, E17 and E142 are replaced each independently with an amino acid residue comprising an aliphatic side chain.

In some embodiments, E16 and E17 are replaced each independently with an amino acid residue comprising an aliphatic side chain, and N18 is replaced with a histidine residue. In some embodiments, E16 and E17 are replaced each independently with an amino acid residue comprising an aliphatic side chain, and R107 is replaced with a lysine residue. In some embodiments, E16 and E17 are replaced each independently with an amino acid residue comprising an aliphatic side chain, and D138 is replaced with an amino acid residue comprising a positively charged side chain.

In some embodiments, E16 and E142 are replaced each independently with an amino acid residue comprising an aliphatic side chain, and N18 is replaced with a histidine residue. In some embodiments, E16 and E142 are replaced each independently with an amino acid residue comprising an aliphatic side chain, and R107 is replaced with a lysine residue. In some embodiments, E16 and E142 are replaced each independently with an amino acid residue comprising an aliphatic side chain, and D138 is replaced with an amino acid residue comprising a positively charged side chain.

In some embodiments, E142 and E17 are replaced each independently with an amino acid residue comprising an aliphatic side chain, and N18 is replaced with a histidine residue. In some embodiments, E142 and E17 are replaced each independently with an amino acid residue comprising an aliphatic side chain, and R107 is replaced with a lysine residue. In some embodiments, E142 and E17 are replaced each independently with an amino acid residue comprising an aliphatic side chain, and D138 is replaced with an amino acid residue comprising a positively charged side chain.

In some embodiments, N18 is replaced with a histidine residue, R107 is replaced with a lysine residue, and E16 is replaced with an amino acid residue comprising an aliphatic side chain. In some embodiments, N18 is replaced with a histidine residue, R107 is replaced with a lysine residue, and E17 is replaced with an amino acid residue comprising an aliphatic side chain. In some embodiments, N18 is replaced with a histidine residue, R107 is replaced with a lysine residue, and E142 is replaced with an amino acid residue comprising an aliphatic side chain. In some embodiments, N18 is replaced with a histidine residue, R107 is replaced with a lysine residue, and D138 is replaced with an amino acid residue comprising a positively charged side chain.

In some embodiments, R107 is replaced with a lysine residue, D138 is replaced with an amino acid residue comprising a positively charged side chain, and E16 is replaced with an amino acid residue comprising an aliphatic side chain. In some embodiments, R107 is replaced with a lysine residue, D138 is replaced with an amino acid residue comprising a positively charged side chain, and E17 is replaced with an amino acid residue comprising an aliphatic side chain. In some embodiments, R107 is replaced with a lysine residue, D138 is replaced with an amino acid residue comprising a positively charged side chain, and E142 is replaced with an amino acid residue comprising an aliphatic side chain.

In some embodiments, N18 is replaced with a histidine residue, D138 is replaced with an amino acid residue comprising a positively charged side chain, and E16 is replaced with an amino acid residue comprising an aliphatic side chain. In some embodiments, N18 is replaced with a histidine residue, D138 is replaced with an amino acid residue comprising a positively charged side chain, and E17 is replaced with an amino acid residue comprising an aliphatic side chain. In some embodiments, N18 is replaced with a histidine residue, D138 is replaced with an amino acid residue comprising a positively charged side chain, and E142 is replaced with an amino acid residue comprising an aliphatic side chain.

In some embodiments, E16, E17 and E142 are replaced each independently with an amino acid residue comprising an aliphatic side chain, and N18 is replaced with a histidine residue. In some embodiments, E16, E17 and E142 are replaced each independently with an amino acid residue comprising an aliphatic side chain, and R107 is replaced with a lysine residue. In some embodiments, E16, E17 and E142 are replaced each independently with an amino acid residue comprising an aliphatic side chain, and D138 is replaced with an amino acid residue comprising a positively charged side chain.

In some embodiments, E16 and E17 are replaced each independently with an amino acid residue comprising an aliphatic side chain, N18 is replaced with a histidine residue, and R107 is replaced with a lysine residue. In some embodiments, E16 and E17 are replaced each independently with an amino acid residue comprising an aliphatic side chain, N18 is replaced with a histidine residue, and D138 is replaced with an amino acid residue comprising a positively charged side chain.

In some embodiments, E16 and E142 are replaced each independently with an amino acid residue comprising an aliphatic side chain, N18 is replaced with a histidine residue, and R107 is replaced with a lysine residue. In some embodiments, E16 and E142 are replaced each independently with an amino acid residue comprising an aliphatic side chain, N18 is replaced with a histidine residue, and D138 is replaced with an amino acid residue comprising a positively charged side chain.

In some embodiments, E142 and E17 are replaced each independently with an amino acid residue comprising an aliphatic side chain, N18 is replaced with a histidine residue, and R107 is replaced with a lysine residue. In some embodiments, E142 and E17 are replaced each independently with an amino acid residue comprising an aliphatic side chain, N18 is replaced with a histidine residue, and D138 is replaced with an amino acid residue comprising a positively charged side chain.

In some embodiments, N18 is replaced with a histidine residue, R107 is replaced with a lysine residue, D138 is replaced with an amino acid residue comprising a positively charged side chain, and E16 is replaced with an amino acid residue comprising an aliphatic side chain. In some embodiments, N18 is replaced with a histidine residue, R107 is replaced with a lysine residue, D138 is replaced with an amino acid residue comprising a positively charged side chain, and E17 is replaced with an amino acid residue comprising an aliphatic side chain. In some embodiments, N18 is replaced with a histidine residue, R107 is replaced with a lysine residue, D138 is replaced with an amino acid residue comprising a positively charged side chain, and E142 is replaced with an amino acid residue comprising an aliphatic side chain.

In some embodiments, E16 is replaced with an amino acid residue comprising an aliphatic side chain, R107 is replaced with a lysine residue, D138 is replaced with an amino acid residue comprising a positively charged side chain, and E17 is replaced with an amino acid residue comprising an aliphatic side chain. In some embodiments, E16 is replaced with an amino acid residue comprising an aliphatic side chain, R107 is replaced with a lysine residue, D138 is replaced with an amino acid residue comprising a positively charged side chain, and E142 is replaced with an amino acid residue comprising an aliphatic side chain. In some embodiments, E16 is replaced with an amino acid residue comprising an aliphatic side chain, R107 is replaced with a lysine residue, D138 is replaced with an amino acid residue comprising a positively charged side chain, and N18 is replaced with a histidine residue.

In some embodiments, E16, E17 and E142 are replaced each independently with an amino acid residue comprising an aliphatic side chain, N18 is replaced with a histidine residue, and R107 is replaced with a lysine residue. In some embodiments, E16, E17 and E142 are replaced each independently with an amino acid residue comprising an aliphatic side chain, N18 is replaced with a histidine residue, and D138 is replaced with an amino acid residue comprising a positively charged side chain.

In some embodiments, E16 and E17 are replaced each independently with an amino acid residue comprising an aliphatic side chain, N18 is replaced with a histidine residue, R107 is replaced with a lysine residue, and D138 is replaced with an amino acid residue comprising a positively charged side chain.

In some embodiments, E16 and E142 are replaced each independently with an amino acid residue comprising an aliphatic side chain, N18 is replaced with a histidine residue, R107 is replaced with a lysine residue, and D138 is replaced with an amino acid residue comprising a positively charged side chain.

In some embodiments, E142 and E17 are replaced each independently with an amino acid residue comprising an aliphatic side chain, N18 is replaced with a histidine residue, R107 is replaced with a lysine residue, and D138 is replaced with an amino acid residue comprising a positively charged side chain.

In some embodiments, E16, E17 and E142 are replaced each independently with an amino acid residue comprising an aliphatic side chain, R107 is replaced with a lysine residue, and D138 is replaced with an amino acid residue comprising a positively charged side chain.

In some embodiments, the polypeptide consists of or comprises a variant of human trypsinogen-1 that is characterized by an amino acid replacement selected from E16A, E17A, N18H, E64K, R107K, K123L, D138K, Y139N, E142L and D147N.

An amino acid replacement E16A in the context of the present specification means that the glutamate residue on position 16 in the amino acid sequence of human wild type trypsinogen-1 (SEQ ID NO 3) is replaced with an alanine residue. This shall apply equally to the other above-described amino acid replacements.

In some embodiments, the polypeptide consists of or comprises a variant of human trypsinogen-1 that is characterized by the amino acid replacements E64K, K123L, Y139N, and D147N, and wherein the variant is further characterized by an amino acid replacement selected from E16A, E17A, N18H, D138K, E142L and R107K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A and E142L. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A and E142L.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E142L and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E142L and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E142L and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements R107K and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A and E142L.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K and E16A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K and E142L. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements R107K, D138K and E16A. In some embodiments, the polypeptide consists of or comprises a variant of human trypsinogen-1 that is characterized by the amino acid replacements E64K, K123L, Y139N, and D147N, and wherein the variant is further characterized by the amino acid replacements R107K, D138K and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements R107K, D138K and E142L.

In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, D138K and E16A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, D138K and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, D138K and E142L.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L and N18H. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, N18H and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, N18H and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L, N18H and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L, N18H and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L, N18H and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L, N18H and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K, D138K and E16A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K, D138K and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements N18H, R107K, D138K and E142L.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, R107K, D138K and E17A. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, R107K, D138K and E142L. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, R107K, D138K and N18H.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L, N18H and R107K. In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L, N18H and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, N18H, R107K and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E142L, N18H, R107K and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E17A, E142L, N18H, R107K and D138K.

In some embodiments, the polypeptide consists of or comprises a variant of human trypsinogen-1 that is characterized by the amino acid replacements E64K, K123L, Y139N, and D147N, and wherein the variant is further characterized by the amino acid replacements E16A, E17A, E142L, R107K and D138K.

In some embodiments, the polypeptide consists of or comprises a variant of human trypsinogen-1 that is characterized by the amino acid replacements E16A, E17A, N18H, E64K, R107K, K123L, D138K, Y139N, E142L and D147N.

In some embodiments, the polypeptide consists of or comprises is a variant of human trypsinogen-1 (SEQ ID NO 3) showing a sequence identity of at least 70%, 80%, 90% or 95% to human trypsinogen-1 (SEQ ID NO 03).

In one embodiment, the polypeptide consists of or comprises a variant characterized by SEQ ID NO 01.

According to a second aspect of the invention, a nucleic acid sequence is provided, wherein the nucleic acid sequence encodes a polypeptide according to the first aspect of the invention.

In one embodiment, the nucleic acid sequence consists of or comprises SEQ ID NO 02 or SEQ ID NO 18.

Where reference is made herein to a polypeptide characterized by a particular sequence, such reference is meant also to encompass polypeptides having an identical function to the particular sequence and 1, 2, 3, 4, 5, 6, 7, 8, 9 or 10 of the amino acid replacements described above, and showing a sequence identity of at least 70%, 80%, 90% or 95% to the certain sequence.

Likewise, where reference is made herein to a nucleic acid sequence characterized by a particular sequence, such reference is meant also to encompass nucleic acid sequences that encode polypeptides having an identical function to the polypeptide encoded by the particular sequence and 1, 2, 3, 4, 5, 6, 7, 8, 9 or 10 of the amino acid replacements described above, and showing a sequence identity of at least 70%, 80%, 90% or 95% to the certain nucleic acid sequence.

In the context of the present specifications the terms "sequence identity" and "percentage of sequence identity" refer to the values determined by comparing two aligned sequences. Methods for alignment of sequences for comparison are well-known in the art. Alignment of sequences for comparison may be conducted by the local homology algorithm of Smith and Waterman, Adv. Appl. Math. 2:482 (1981), by the global alignment algorithm of Needleman and Wunsch, J. Mol. Biol. 48:443 (1970), by the search for similarity method of Pearson and Lipman, Proc. Nat. Acad. Sci. 85:2444 (1988) or by computerized implementations of these algorithms, including, but not limited to: CLUSTAL, GAP, BESTFIT, BLAST, FASTA and TFASTA. Unless otherwise stated, sequence identity values provided herein refer to the value obtained using the BLAST suite of programs using default parameters (Altschul et al., J. Mol. Biol. 215:403-410 (1990)). Software for performing BLAST analyses is publicly available, e.g., through the National Center for Biotechnology-Information (http://blast.ncbi.nlm.nih.gov/). One example for comparison of amino acid sequences is the BLASTP algorithm that uses default settings such as: Expect threshold: 10; Word size: 3; Max matches in a query range: 0; Matrix: BLOSUM62; Gap Costs: Existence 11, Extension 1; Compositional adjustments: Conditional compositional score matrix adjustment. One such example for comparison of nucleic acid sequences is the BLASTN algorithm that uses the default settings: Expect threshold: 10; Word size: 28; Max matches in a query range: 0; Match/Mismatch Scores: 1.-2; Gap costs: Linear According to a third aspect of the invention, a host cell comprising a nucleic acid sequence according to the second aspect of the invention is provided.

In some embodiments, the nucleic acid sequence is a transgene to the host cell.

The term "transgene" in the context of the present specification refers to a nucleic acid sequence that has been transferred into the host cell from another organism.

In some embodiments, the nucleic acid sequence is comprised within a vector operable in the host cell.

In some embodiments, the vector consists of or comprises a nucleic acid sequence characterized by SEQ ID NO 18.

The term "vector operable in the host cell" in the context of the present specification refers to a DNA molecule that can be used as a vehicle for transporting a foreign nucleic acid sequence into the host cell, wherein such DNA molecule can be replicated in the host cell, and wherein the foreign nucleic acid sequence comprised within the DNA molecule can be expressed in the host cell.

In some embodiments, the host cell is selected from the group comprised of a member of the genus *Escherichia* such as *E. coli*, a member of the genus *Saccharomyces* such as *S. cerevisiae*, a member of the genus *Schizosaccharomyces* such as *S. pombe*, a member of the genus *Pichia* such as *P. pastoris*, a member of the genus *Aspergillus* such as *A. niger*, a member of the genus *Bacillus* such as *B. subtilis* and a mammalian cell in cell culture such as a CHO (Chinese hamster ovary) cell or a HEK (Human Embryonic Kidney) 293 cell.

According to a fourth aspect of the invention, a method for manufacturing a polypeptide according to the first aspect of the invention is provided, wherein the method comprises the use of a host cell according to the fourth aspect of the invention.

In some embodiments, the method comprises:
  a propagation step, wherein the host cell is propagated, and
  an expression step, wherein the nucleic acid sequence is expressed in the host cell yielding a polypeptide according to the first aspect of the invention.

The polypeptide may be located intracellularly or may be transported to the periplasma or the extracellular space, particularly by use a of N- or C-terminal signal peptide attached to the polypeptide.

According to a fifth aspect of the invention, a method for quantifying an analyte is provided, wherein the method comprises the steps of:
  providing a reaction volume,
  adding to the reaction volume in a first step an analyte and a first ligand being able to specifically bind the analyte with a dissociation constant equal or below $10^{-6}$ mol/L, $10^{-7}$ mol/L, $10^{-8}$ mol/L or $10^{-9}$ mol/L,
  adding to the reaction volume in a second step a second ligand able to specifically bind the first ligand with a dissociation constant equal or below $10^{-6}$ mol/L, $10^{-7}$ mol/L, $10^{-8}$ mol/L or $10^{-9}$ mol/L, wherein the second ligand comprises a first polypeptide having a proteolytic activity,
  adding to the reaction volume in a third step a precursor polypeptide, wherein the precursor polypeptide is cleavable by the first polypeptide into a second polypeptide, and a peptide substrate of the second polypeptide comprising a luminescent first FRET partner and a second FRET partner, wherein the first FRET partner and the second FRET partner are able to interact in such a way that the luminescent signal of the first FRET partner is changed with spatial approximation of the first FRET partner and the second FRET partner, and wherein the peptide substrate is cleavable by the second polypeptide between the first FRET partner and the second FRET partner, wherein cleavage of the peptide substrate leads to a change in the spatial approximation of the first and the second FRET partner,
  quantifying the amount of the analyte by measurement of the luminescence of the first FRET partner and/or the second FRET partner,
  characterized in that the precursor polypeptide is a polypeptide according to the first aspect of the invention.

In some embodiments, the method for quantifying an analyte is provided, wherein the method comprises the steps of
  providing a surface defining a reaction volume,
  adding to the reaction volume an analyte capable of binding specifically, or capable absorbing unspecifically, to said surface, in a first step, then
  adding a first ligand able to specifically bind to the analyte with a dissociation constant equal or below $10^{-6}$ mol/L, $10^{-7}$ mol/L, $10^{-8}$ mol/L or $10^{-9}$ mol/L in a second step,
  adding to the reaction volume a second ligand able to bind specifically to the first ligand with a dissociation constant equal or below $10^{-6}$ mol/L, $10^{-7}$ mol/L, $10^{-8}$ mol/L or $10^{-9}$ mol/L in a third step, wherein the second ligand comprises a first polypeptide having a proteolytic activity,
  washing the surface, so that unbound components are washed away and only second ligand molecules and first polypeptides comprised therein remain bound to said surface;
  adding to the reaction volume, in a fourth step a precursor polypeptide, wherein the precursor polypeptide is cleavable by the first polypeptide into a second polypeptide, and a peptide substrate of the second polypeptide comprising a luminescent first FRET partner and a second FRET partner, wherein the first FRET partner and the second FRET partner are able to interact in such a way that the luminescent signal of the first FRET partner is changed with spatial approximation of the first FRET partner and the second FRET partner, and wherein the peptide substrate is cleavable by the second polypeptide between the first FRET partner and the second FRET partner, wherein cleavage of the peptide substrate leads to a change in the spatial approximation of the first and the second FRET partner,
  quantifying the amount of the analyte by measurement of the luminescence of the first FRET partner and/or the second FRET partner,
  characterized in that the precursor polypeptide is a polypeptide according to the first aspect of the invention.

According to an alternative of the above aspect of the invention, a method for quantifying an analyte is provided, wherein the method comprises the steps of:
  providing a reaction volume,
  adding to the reaction volume in a first step an analyte and a first ligand being able to specifically bind the analyte with a dissociation constant equal or below $10^{-6}$ mol/L, $10^{-7}$ mol/L, $10^{-8}$ mol/L or $10^{-9}$ mol/L, wherein the first ligand comprises a first polypeptide having a proteolytic activity, adding to the reaction volume in a second step a precursor polypeptide, wherein the precursor polypeptide is cleavable by the first polypeptide into a second polypeptide, and a peptide substrate of the second polypeptide comprising a luminescent first FRET partner and a second FRET partner, wherein the first FRET partner and the second FRET partner are able to interact in such a way that the luminescent signal of the first FRET partner is changed with spatial approximation of the first FRET partner and the second FRET partner, and wherein the peptide substrate is cleavable by the second polypeptide between the first FRET partner and the second FRET partner, wherein cleavage of the peptide substrate leads to a change in the spatial approximation of the first and the second FRET partner, quantifying the amount of the analyte by measurement of the luminescence of the first FRET partner and/or the second FRET partner, characterized in that the precursor polypeptide is a polypeptide according to the first aspect of the invention.

In some embodiments, the method for quantifying an analyte is provided, wherein the method comprises the steps of:

providing a surface defining a reaction volume, adding to the reaction volume an analyte capable of binding specifically, or capable absorbing unspecifically, to said surface, in a first step, then adding a first ligand able to specifically bind to the analyte with a dissociation constant equal or below $10^{-6}$ mol/L, $10^{-7}$ mol/L, $10^{-8}$ mol/L or $10^{-9}$ mol/L in a second step, wherein the first ligand comprises a first polypeptide having a proteolyitc activity, washing the surface, so that unbound components are washed away and only second ligand molecules and first polypeptides comprised therein remain bound to said surface;

adding to the reaction volume, in a third step a precursor polypeptide, wherein the precursor polypeptide is cleavable by the first polypeptide into a second polypeptide, and a peptide substrate of the second polypeptide comprising a luminescent first FRET partner and a second FRET partner, wherein the first FRET partner and the second FRET partner are able to interact in such a way that the luminescent signal of the first FRET partner is changed with spatial approximation of the first FRET partner and the second FRET partner, and wherein the peptide substrate is cleavable by the second polypeptide between the first FRET partner and the second FRET partner, wherein cleavage of the peptide substrate leads to a change in the spatial approximation of the first and the second FRET partner, quantifying the amount of the analyte by measurement of the luminescence of the first FRET partner and/or the second FRET partner, characterized in that the precursor polypeptide is a polypeptide according to the first aspect of the invention.

The term "a first polypeptide having a proteolytic activity" particularly refers to a protease or a polypeptide comprising such protease, wherein the precursor polypeptide is a substrate of the protease, and wherein particularly the protease cleaves the precursor polypeptide into an activation peptide and the second polypeptide.

The term "peptide substrate cleavable by the second polypeptide between the first FRET partner and the second FRET partner" particularly means that the peptide substrate is a substrate of the second polypeptide, and that the first FRET partner is bound to a first amino acid residue of the peptide substrate, and the second FRET partner is bound to a second amino acid residue of the peptide substrate, wherein the first amino acid residue and the second amino acid residue are connected by at least one peptide bond, and wherein this peptide bond specifically is cleaved by the second polypeptide.

The term "substrate" in the context of the present specification particularly refers to a compound that is bound and converted by an enzyme, for example a protease, particularly by the first polypeptide or the second polypeptide described above, with a $K_M$ of not larger than 100 mmol/L, 50 mmol/L, 20 mmol/L, 10 mmol/L, 5 mmol/L, 1 mmol/L or 0.1 mmol/L.

One advantage of the use of the polypeptide according to the invention is that due to the decreased autoactivation of the polypeptide, the background signal of the method of the invention is decreased, resulting in a lowered detection or quantification limit.

A ligand according to any aspect or embodiment of the invention may be any molecule that binds to a target molecule or analyte with high affinity and specificity. Such a ligand may be an antibody, an antibody fragment, an antibody-like molecule or a nucleic acid aptamer molecule of 10 to 75 nucleotides in length, any of which binds to the target molecule.

High affinity in the context of the present specification refers to the dissociation constant of the binding of the ligand to the target molecule, wherein the dissociation constant is $10^{-6}$ mol/L, $10^{-7}$ mol/L, $10^{-8}$ mol/L or $10^{-8}$ mol/l or less, and wherein the ligand does not bind to control molecules, for example proteins, with unrelated structural features. Control molecules are, by way of non-limiting example, plasma proteins such as albumins, globulins, lipoproteins, fibrinogens, prothrombin, acute phase proteins, tumour markers such as CEA, CA19-9 or AFP and transferrin.

High specificity in the context of the present specification refers to the ratio of properly detected targets or analytes and the sum of all detected compounds or substances, wherein the ratio is 80%, 85%, 90%, 95%, 99% or 99.9%.

An antibody fragment may be a Fab fragment, which is the antigen-binding fragment of an antibody, or a single-chain variable fragment, which is a fusion protein of the variable regions of the heavy and the light chain of an antibody connected by a peptide linker. An antibody-like molecule may be a repeat protein, such as a designed ankyrin repeat protein (Molecular Partners, Zürich).

Suitable ligands according to the above aspect of the invention may also be developed by evolutiv methods such as phage display, ribosome display or SELEX, wherein polypeptide or oligonucleotides are selected due to their binding affinity to a target of interest. Additionally, the binding affinity of an identified ligand may be improved by cycles of evolution of the amino acid sequence or nucleotide sequence, and selection of the evolved inhibitors may be effected based on the required affinity.

The term "analyte" in the context of the present specification particularly refers to a compound or substance of interest that is a target of an analysis.

In some embodiments, the first polypeptide is characterized by a $K_M$ value of not larger than 10 mmol/L for the precursor polypeptide as substrate.

In some embodiments, the first FRET-Partner is coupled to the N-terminus or the C-terminus of the peptide substrate.

In some embodiments, the second FRET partner is coupled to the N-terminus or the C-terminus of the peptide substrate. In some embodiments, the first FRET partner is coupled to the N-terminus of the peptide substrate, and the second FRET partner is coupled to the C-terminus of the peptide substrate. In some embodiments, the first FRET partner is coupled to the C-terminus of the peptide substrate, and the second FRET partner is coupled to the N-terminus of the peptide substrate.

In some embodiments, the analyte is selected from a peptide, a polypeptide, a nucleic acid and a small molecule such as a lipid, a sugar or a metabolite.

In some embodiments, the first and/or the second ligand is selected from an antibody, an antibody fragment, an antibody-like molecule and nucleic acid aptamer molecule of 10 to 75 nucleotides in length.

In some embodiments, the peptide substrate is or comprises a peptide characterized by an amino acid sequence selected from SEQ ID NO 06, SEQ ID NO 07, SEQ ID NO 08, SEQ ID NO 09, SEQ ID NO 10, SEQ ID NO 11, SEQ ID NO 12, SEQ ID NO 13, SEQ ID NO 14, SEQ ID NO 15, SEQ ID NO 16 and SEQ ID NO 17.

In some embodiments, the first polypeptide having a proteolytic activity is or comprises the human enteropeptidase catalytic light chain (Uniprot E9PG70) or a polypeptide characterized by SEQ ID NO 05 (supercharged variant of human enteropeptidase).

In some embodiments, the first FRET partner is a dye comprising a lanthanide atom.

In some embodiments, the first FRET partner is a dye comprising a europium atom or a terbium atom.

In some embodiments, the first FRET partner is selected from fluorescein (CAS No. 2321-07-5) and EuL[H] (Eu(III) [2-[2-[bis(carboxymethyl)amino]ethyl-[2-[carboxy-methyl-[2-oxo-2-[4-[2-(1,10-phenanthrolin-2-yl)ethynyl]anilino] ethyl]amino]ethyl]amino]-acetate]).

In some embodiments, the second FRET partner is Atto612Q, Cy5 (6-[3,3-dimethyl-2-[(1E,3E,5E)-5-(1,3,3-trimethylindolin-2-ylidene)penta-1,3-dienyl]indol-1-ium-1-yl]hexanoic acid) or TAMRA (Carboxy-tetramethylrhodamine).

In some embodiments, the second FRET partner is not luminescent.

In one embodiment, the second FRET partner is a dark quencher, particularly a black hole quencher such as BHQ-0 (Biosearch Technologies, USA), BHQ-1 (Biosearch Technologies, USA), BHQ-2 (Biosearch Technologies, USA), BHQ-3 (Biosearch Technologies, USA) or BHQ-10 (2-[(E)-[4-[(4-hydroxy-4-oxo-butyl)-methyl-amino]phenyl]azo]-5-[(E)-(4-oxoniosulfonylphenyl)azo]benzenesulfonate), Dabysyl (dimethylaminoazobenzenesulfonic acid), a Qxl quencher such as QXL 490 (AnaSpec, Inc., USA), QXL 570 (AnaSpec, Inc., USA), QXL 610 (AnaSpec, Inc., USA), QXL 670 (AnaSpec Inc., USA) or QXL 680 (AnaSpec, Inc., USA), Iowa black FQ (Integrated DNA Technologies, Inc., USA), Iowa black RQ (Integrated DNA Technologies, Inc., USA), IRDye QC-1 (LI-COR Biosciences GmbH, Germany) or Eclipse Dark Quencher (Eurogentec Deutschland GmbH, Germany).

In some embodiments, the first FRET partner is EuL[H] and the second FRET Partner is BHQ-10. In some embodiments, EuL[H] is coupled to the N-terminus of the substrate peptide, and BHQ-10 is coupled to the C-terminus of the substrate peptide.

In some embodiments, the first FRET partner is fluorescein and the second FRET partner is TAMRA. In some embodiments, TAMRA is coupled to the N-terminus of the substrate peptide, and fluorescein is coupled to the C-terminus of the substrate peptide.

The invention is further illustrated by the following examples and figures, from which further embodiments and advantages can be drawn. These examples are meant to illustrate the invention but not to limit its scope.

Wherever alternatives for single separable features such as, for example, a variant or a nucleic acid sequence coding a variant, are laid out herein as "embodiments", it is to be understood that such alternatives may be combined freely to form discrete embodiments of the invention disclosed herein.

DESCRIPTION OF THE FIGURES

FIG. 3 shows a comparison of the amino acid sequences of the polypeptide of the invention and human wild type trypsinogen, wherein modified amino acids are highlighted in bold letters.

FIG. 4 shows a comparison of the nucleic acid sequences of the polypeptide of the invention and human wild type trypsinogen, wherein modified nucleic acids are highlighted in bold letters.

EXAMPLES

Figure 1:
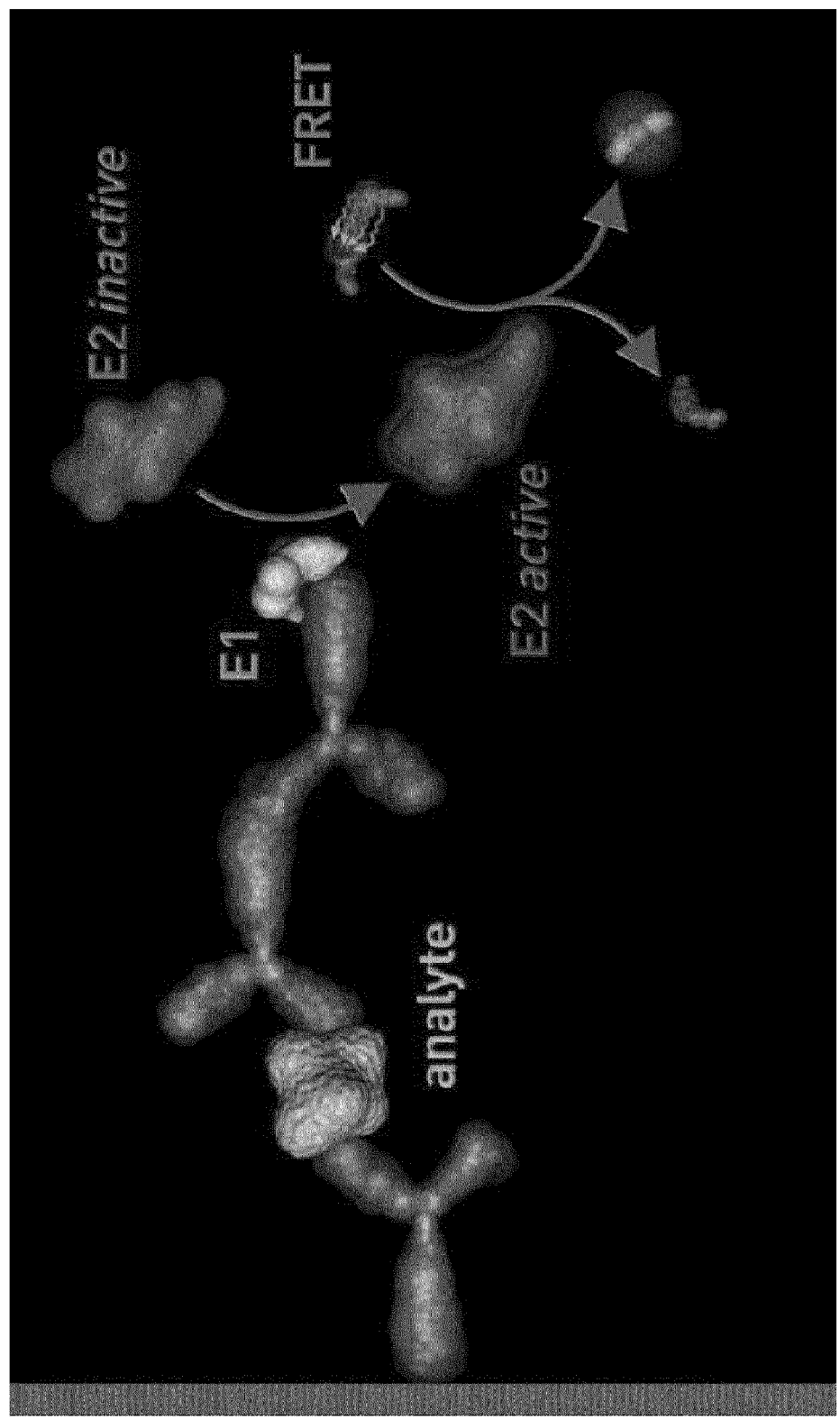
FIG. 1 shows the principle of a method of the invention.

Example 1: Manufacture of the Supercharged Variant of Human Trypsinogen

The supercharged variant of human trypsinogen-1 manufactured in E. coli BL21. Briefly, E. coli BL21 cells comprising an expression vector characterized by SEQ ID NO 17 were propagated in a TB-medium with 30 µg/ml Kanamycin at 37° C. until a OD600 of 0.8 to 1 was reached. Then the expression was induced by adding 1 mM IPTG. Parallel to that glucose was added to a final concentration of 1% (w/v). Then, the cells were incubated for 18 h at 25° C. After incubation the cells were harvested and the resulting cell pellets were stored at −20° C.

For workup, the cells were resuspended in cell lysis buffer (1 mmol/L EDTA; 100 mmol/L Tris/HCl; pH 7.0). To the cell suspension 5 mg lysozyme was added. Following this, the MgCl$_2$ concentration of the suspension was adjusted to 3 mmol/L, and DNAse I was added to a final concentration of 10 µg/mL. The suspension was then incubated at 24° C. for 30 min. The cells were then mechanically disrupted in a high pressure homogenizer, wherein the cell disruption was performed three times at a pressure of approx. 1000 bar. The disrupted cells were incubated for 30 min at 24° C. and centrifuged.

The inclusion bodies comprising the supercharged variant were prepared from the insoluble fraction of the cell disruption as following: The inclusion bodies were resuspended in IB-washing buffer I (20 mmol/L EDTA pH 8.0; 500 mmol/L NaCl; 2% Triton X-100), stirred for 30 min at room temperature and centrifuged 30 min at 20,000 g. The resulting pellet was washed again with IB-washing buffer I and twice with IB-washing buffer (20 mmol/L EDTA; 100 mmol/L Tris/HCl; pH 7.0) accordingly, but without stirring.

The inclusion bodies were solubilised in 4 mol/L guanidinium, 100 mmol/L TRIS HCl and 5 mmol/L EDTA, pH 8.0, reduced with 3 mol/L dithiothreitol and refolded via fast dilution method in a refolding buffer (0.7 mol/L arginine, 1 mmol/L EDTA, 3 mmol/L reduced glutathione, 3 mmol/L oxized glutathione, pH 8.6). The refolded supercharged variant was subsequently purified via an ecotin-affinity column.

Example 2: Characterization of the Supercharged Variant of Human Trypsinogen

Figure 2:
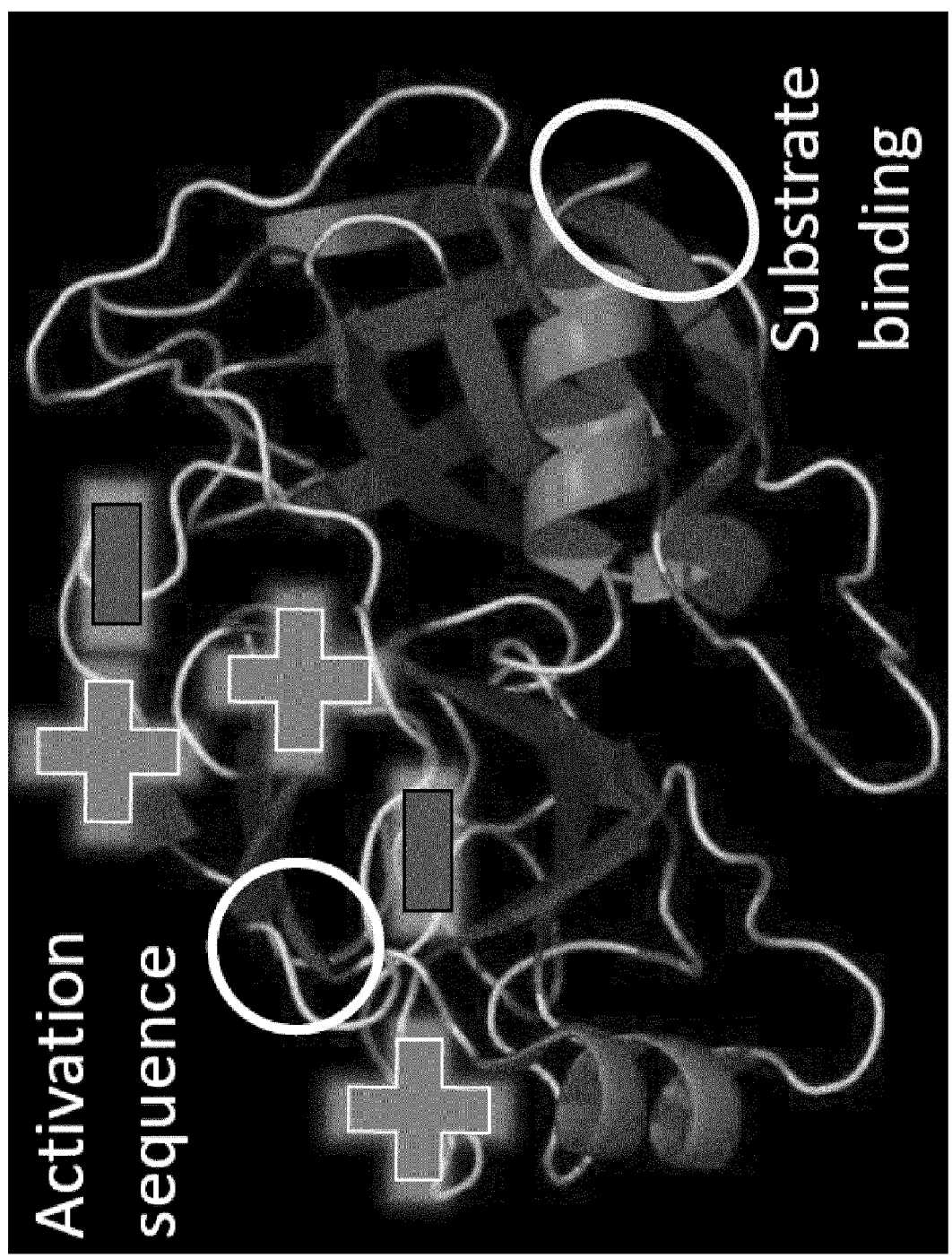
FIG. 2 shows a schematic of the human trypsinogen variant with lower autoactivation.
Figure 6:
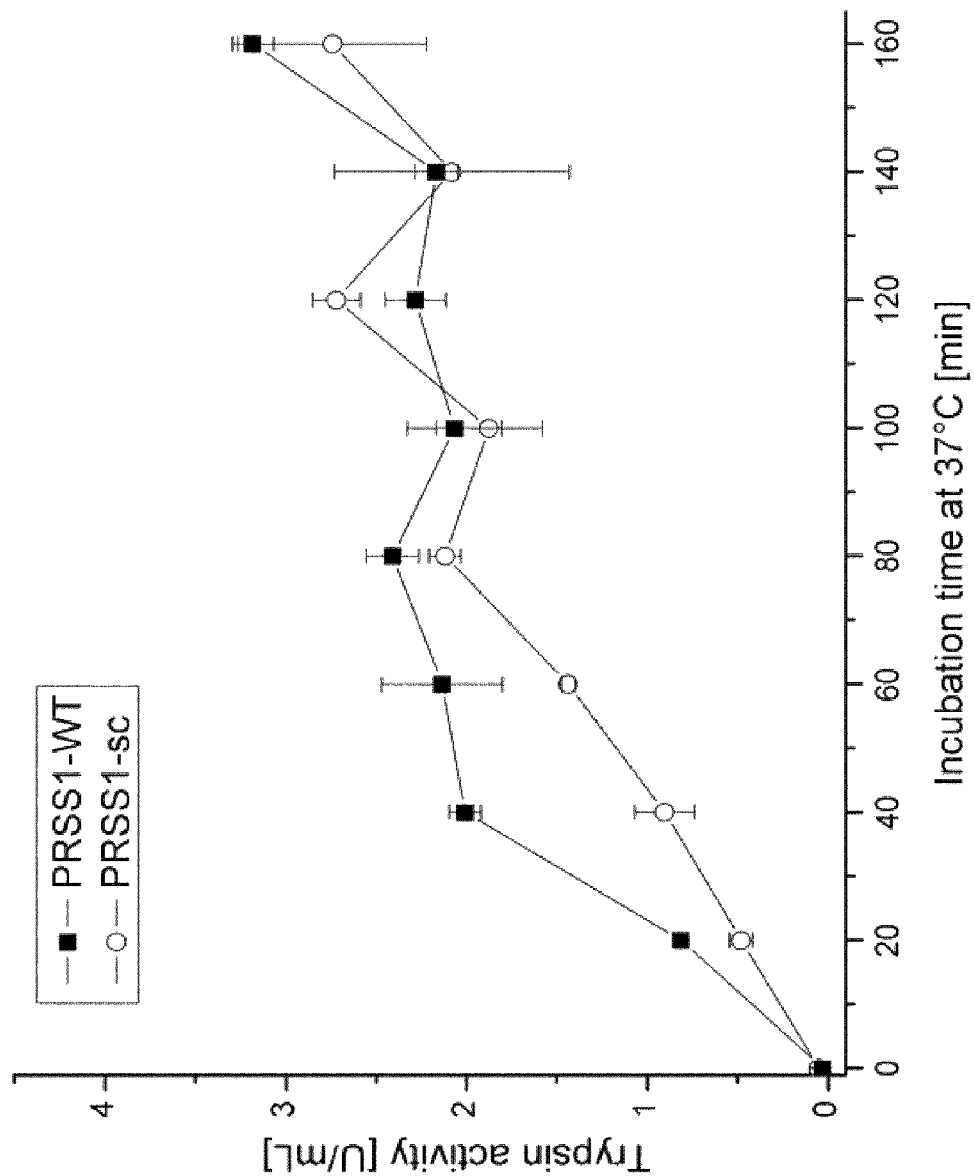
FIG. 6 shows kinetics of PRSS1 sc- and PRSS1 wt-activation after incubation with human enteropeptidase (hEPI-Sc-C112S), wherein the trypsin activity is plotted versus the incubation time.

The human trypsinogen mutant with lower autoactivation is based on the introduction of charged amino acids on the protein surface close to the activation site (FIG. 2). PRSS1 sc (SEQ ID NO 01) does not show a significant autoactivation, as shown in FIG. 3 (activation of trypsinogen (2 µM) occurred with 10 nmol/L trypsin in 100 mmol/L Tris/HCl pH 8, 1 mmol/L CaCl$_2$. Substrate CBZ(carbobenzoxy)-GPR-pNA (para-nitroaniline) was incubated for 5 min at 25° C.), and in FIG. 6 (trypsinogen (100 nmol/L) was incubated in 100 mmol/L Tris pH 8.0 for 2 hours at 37° C. As a substrate, a peptide with the sequence TAMRA-GSRC(Fluorescein)-NH2 was used (peptide 7, SEQ ID NO 10).

Figure 5:
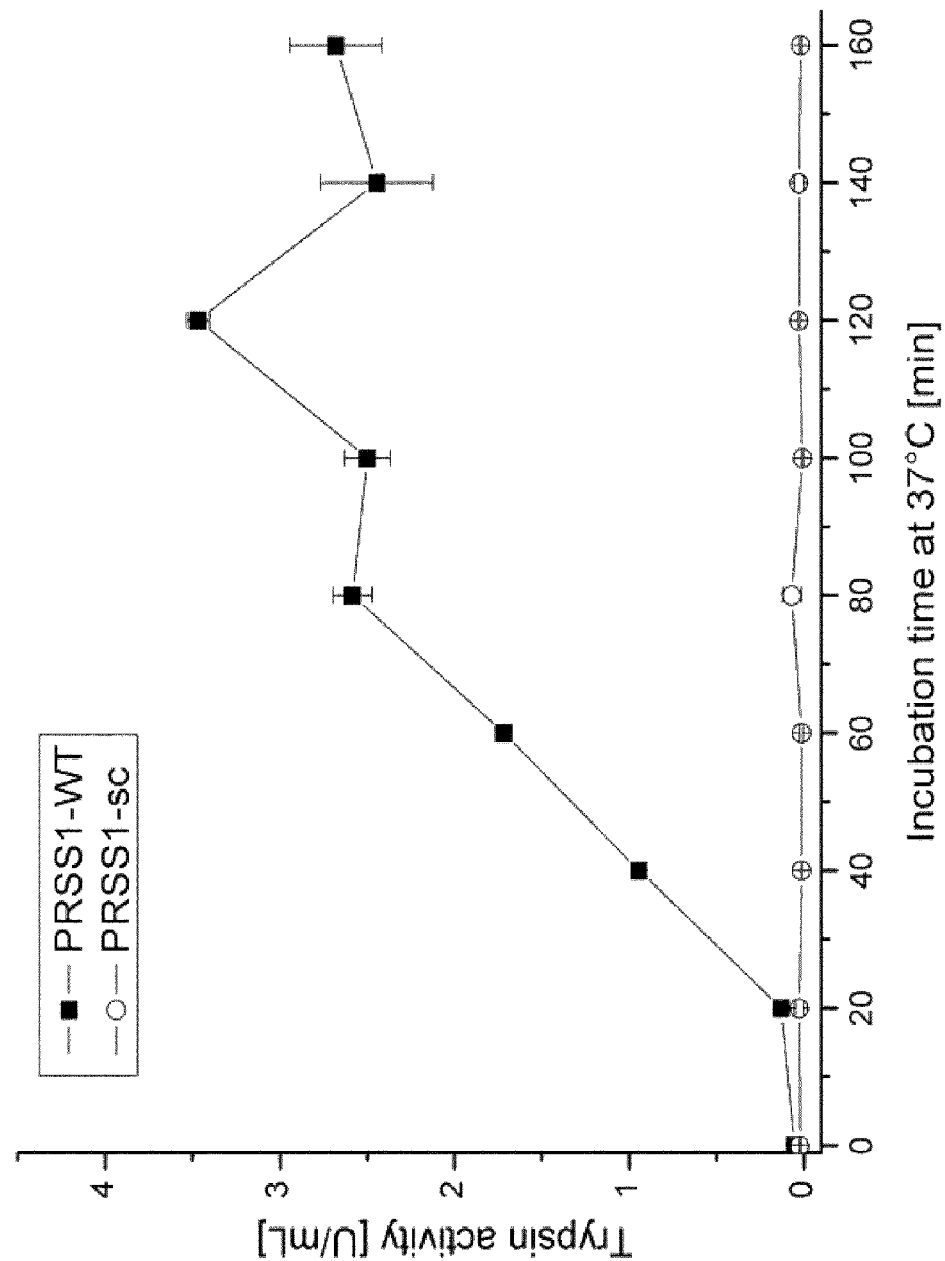
FIG. 5 shows the autoactivation kinetics of PRSS1 sc in comparison to PRSS1 wt, wherein the trypsin activity is plotted versus the incubation time.

An analysis with SDS-Gelelectrophoresis showed similar results, as shown in FIG. 5 (SDS-PAGE of autoactivation of PRSS1-WT and PRSS1-sc. Activation of trypsinogen (2 µmol/L) occurred with 10 nmol/L trypsin in 100 mmol/L Tris/HCl pH 8, 1 mmol/L CaCl$_2$. Silver staining was used for visualization).

Figure 7:
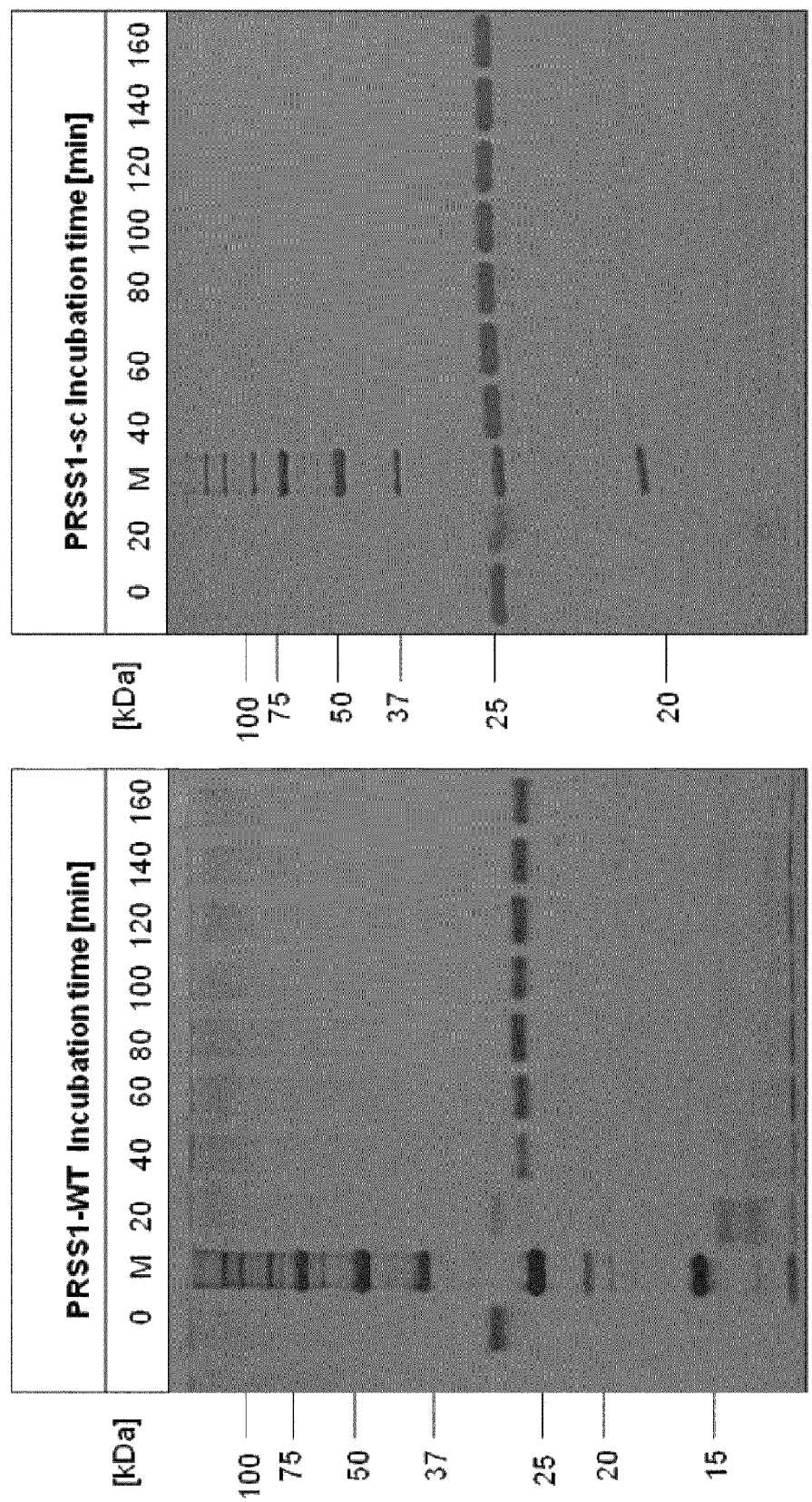
FIG. 7 shows SDS-PAGE gels of autoactivation of PRSS1-WT and PRSS1-sc.
Figure 8:
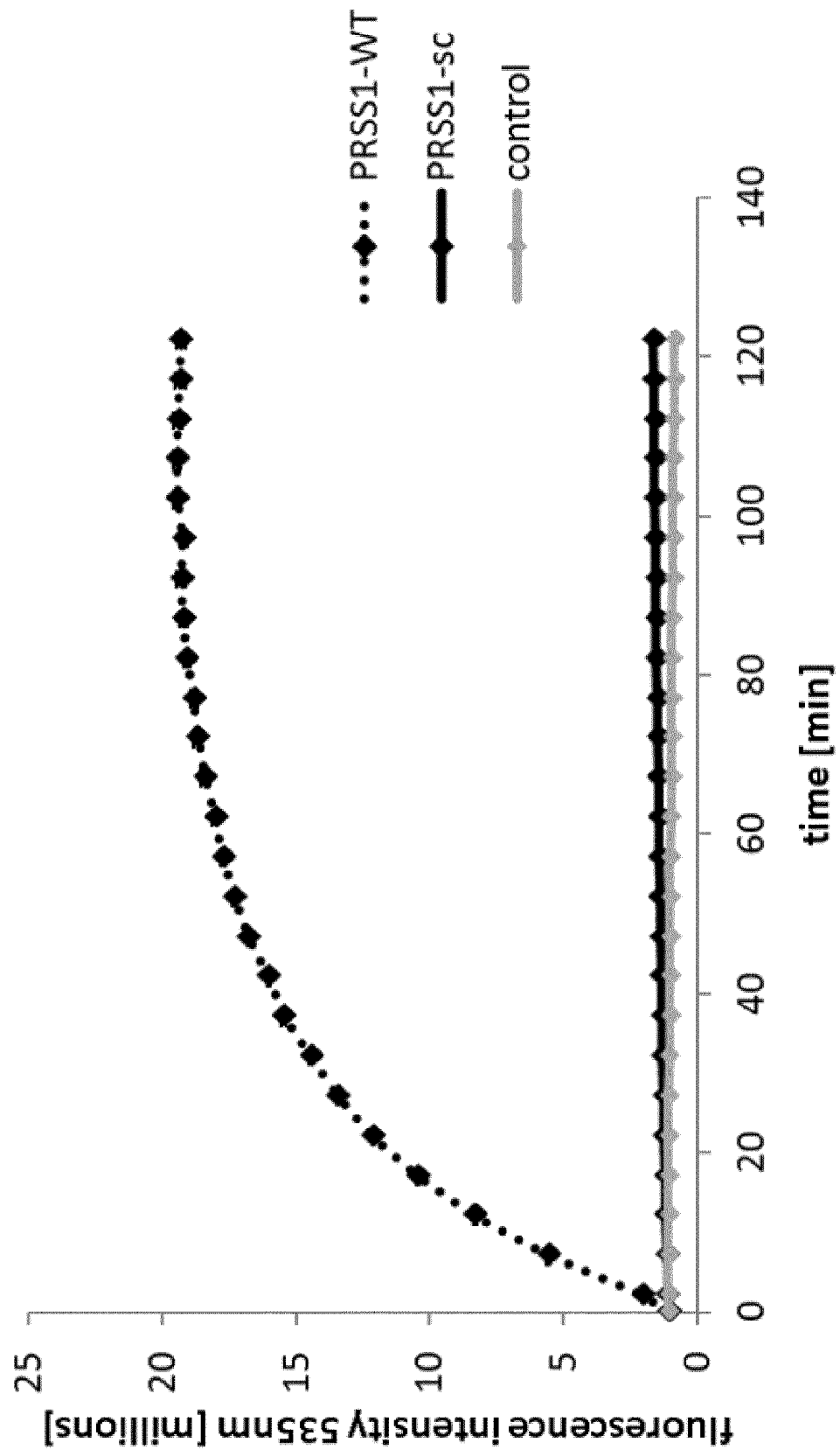
FIG. 8 shows the autoactivation kinetics of PRSS1 sc in comparison to PRSS1 wt, wherein the fluorescence intensity is plotted versus the incubation time.
Figure 9:
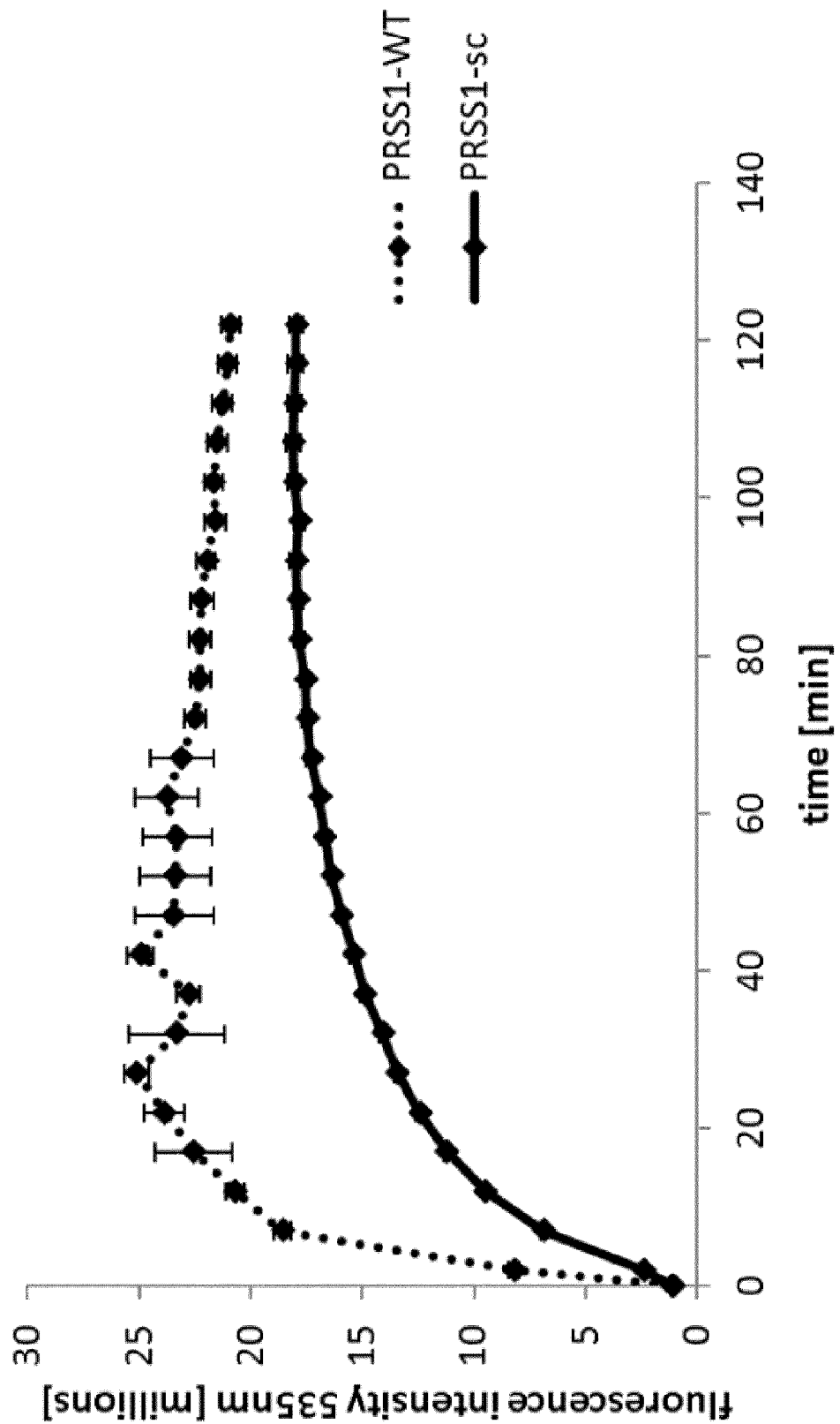
FIG. 9 shows kinetics of PRSS1 sc- and PRSS1 wt-activation after incubation with human enteropeptidase (hEPI-Sc-C112S), wherein the fluorescence intensity is plotted versus the incubation time.

Both PRSS1 versions can be activated to similar levels, although PRSS1 sc shows a slightly slower activation profile as shown in FIG. 4 (activation of trypsinogen (2 µmol/L) occurred with 1 nmol/L hEPI-sc-C112S in 100 mmol/L Tris/HCl pH 8, 1 mmol/L CaCl$_2$. Substrate CBZ-GPR-pNA was incubated for 5 min at 25° C.), and FIG. 7 (activation of trypsinogen (100 nmol/L) occurred with 100 pmol/L hEPI-sc-C112S in 100 mmol/L Tris pH 8.0 for 2 hours at 37° C. As a substrate, a peptide with the sequence TAMRA-GSRC(Fluorescein)-NH$_2$ was used (peptide 7, SEQ ID NO 10)).

Table 1 shows the enzyme kinetics ($K_M$, $K_{cat}$) of PRSS1 sc in comparison to RSS1 wt. Both enzymes were activated by human enteropeptidase (hEPI-Sc-C112S) for 200 min at 37° C. in 100 mmol/L Tris-HCl (pH 8.0), 1 mmol/L CaCl$_2$. Assays were performed in 100 mmol/L Tris-HCl (pH 8.0) 1 mmol/L CaCl$_2$ and 10 µmol/L to 1000 µmol/L CBZ-GPR-pNA at room temperature. The reaction was started by adding PRSS1 variants (12.5 ng) and monitored continuously for 5 min by increasing absorbance at 405 nm (extinction coefficient for p-nitroaniline ε=10092 L/mol/cm).

TABLE 1

|  | $v_{max}$ [µmol/L/min] | $K_M$ [µmol/L] | $k_{cat}$ [s-1] | $k_{cat}/K_M$ [L/µmol/s] |
| --- | --- | --- | --- | --- |
| PRSS1-WT | 100.8 ± 4.4 | 78.0 ± 12.2 | 324.1 ± 13.8 | 4.7 ± 0.5 |
| PRSS1-sc | 152.3 ± 5.9 | 129.8 ± 8.4 | 489.0 ± 18.9 | 3.7 ± 0.3 |

Figure 11:
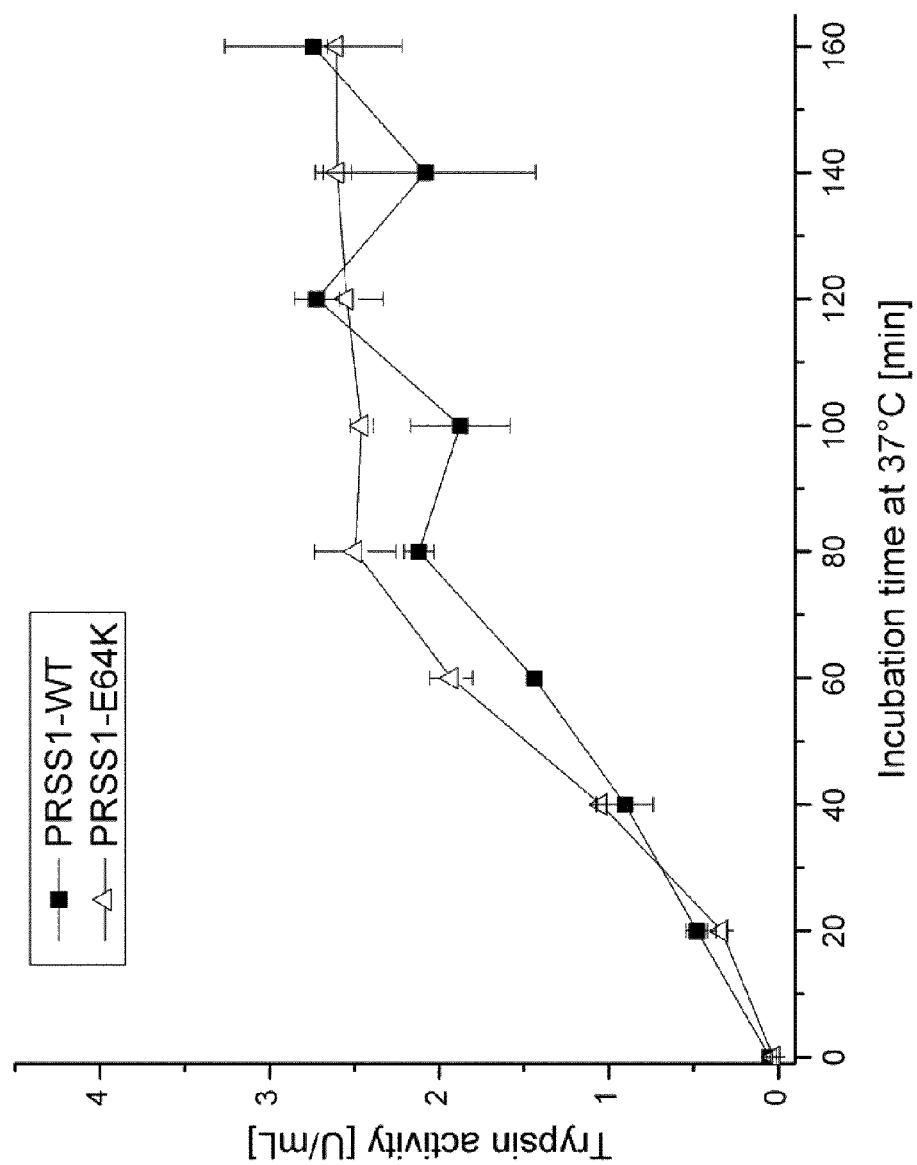
FIG. 11 shows the autoactivation kinetics of PRSS1 E64K in comparison to PRSS1 wt, wherein the trypsin activity is plotted versus the incubation time

The autoactivation kinetics of PRSS1 E64K is not significantly different to that of PRSS1 wt. This means that the mutation E64K alone is not responsible for the reduced autoactivation of scPRSS1 but contributes to the overall change in the surface charge of the protein and thereby contributes to the reduced autoactivation observed in PRSS1-sc (FIG. 11).

Example 3: Sandwich Assay with the Supercharged Variant of Human Trypsinogen

FIG. 1 shows the principle of an assay of the invention. In this assay, an analyte is bound by a primary antibody, which is specific for the analyte. After a wash step, the primary antibody is bound by a secondary antibody that is covalently coupled to enteropeptidase (E1). Then, again after a further wash step, a mixture of inactive trypsinogen and a FRET-peptide (peptide 7, SEQ ID NO 10, with fluorescein as donor dye and TAMRA as acceptor dye) is added to the assay, wherein the antibody-bound enteropeptidase activates inactive trypsinogen (E2 inactive) into active trypsin, and trypsin then cleaves the FRET-peptide, resulting in a signal increase of the donor dye (fluorescein).

Figure 10:
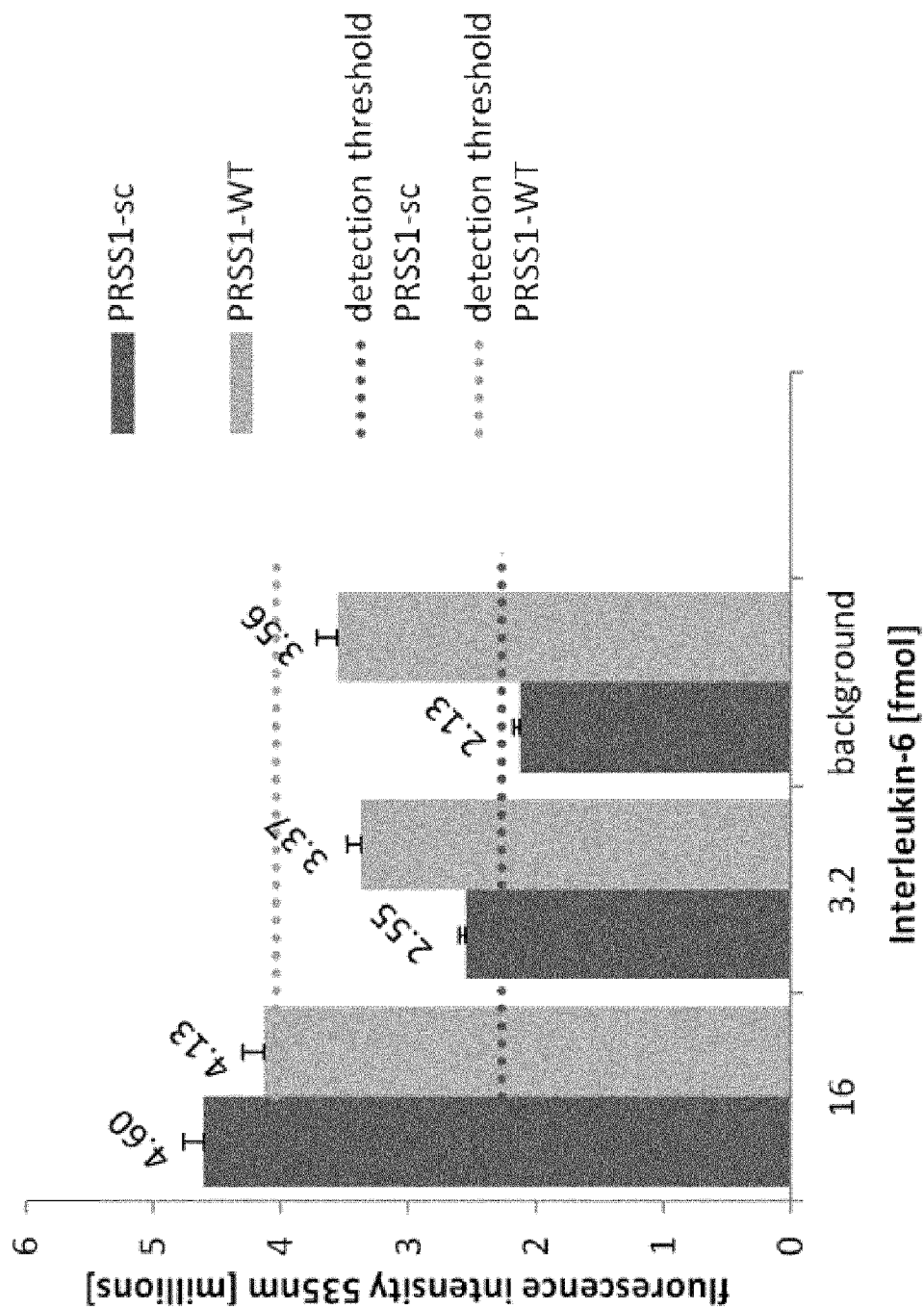
FIG. 10 shows an indirect ELISA against human interleukin-6 (IL-6), wherein the fluorescence intensity is plotted versus the interleukin-6 concentration.

FIG. 10 shows the results of such an ELISA. A primary antibody against IL-6 was detected with a secondary antibody which was labelled with human enterpeptidase light chain sc C112S. The FRET peptide substrate was cleaved by either PRSS1-WT or PRSS1-sc. The detection limit with PRSS1-sc is at least five times lower than with PRSS1-WT. This is due to the lower background signal of PRSS1-sc. The assay was performed in 100 mmol/L TRIS at pH 8.0. After binding of the secondary antibody 100 nmol/L trypsinogen (WT or sc) and 100 nmol/L peptide substrate 7 [TAMRA-GSRC(Fluorescein)-NH$_2$ (peptide 7, SEQ ID NO 10)) were added and incubated for 60 min at 37° C. The resulting fluorescence intensity was then recorded.

The invention claimed is:

1. A polypeptide comprising a variant of human wild-type trypsinogen-1,
   comprising the substitutions:
   amino acid residue E64 is replaced with an amino acid residue comprising a positively charged side chain,
   amino acid residue K123 is replaced with an amino acid residue comprising an aliphatic side chain and
   amino acid residues Y139 and D147 are replaced with a glutamine or asparagine residue,
   an amino acid residue selected from E16, E17 and E142 is replaced with an amino acid residue comprising an aliphatic side chain, and/or
   amino acid residue N18 is replaced with a histidine residue, and/or
   amino acid residue R107 is replaced with a lysine residue, and/or
   amino acid residue D138 is replaced with an amino acid residue comprising a positively charged side chain,
   wherein said variant is cleavable into a polypeptide having enzymatic activity when compared to human trypsin-1; and wherein the positions of the amino acid replacements refer to the amino acid sequence of human wild-type trypsinogen-1 according of SEQ ID NO: 3.

2. The polypeptide according to claim 1, wherein all of E16, E17, and E142 are replaced each independently with an amino acid residue comprising an aliphatic side chain.

3. The polypeptide according to claim 1, wherein said variant comprises an amino acid replacement selected from E16A, E17A, N18H, E64K, R107K, K123L, D138K, Y139N, E142L and D147N.

4. A polypeptide comprising SEQ ID NO 01.

5. A nucleic acid sequence encoding a polypeptide according to claim 1.

6. The nucleic acid sequence according to claim 5, comprising SEQ ID NO 02 or SEQ ID NO 18.

7. A host cell comprising a nucleic acid sequence according to claim 5.

8. A method for manufacturing a polypeptide according to claim 1, comprising use of a host cell comprising a nucleic acid encoding the polypeptide.

9. A method for quantifying an analyte, comprising the steps of:
   providing a reaction volume,
   adding to said reaction volume in a first step an analyte and a first ligand able to specifically bind to said analyte with a dissociation constant equal or below $10^{-6}$ mol/L, $10^{-7}$ mol/L, $10^{-8}$ mol/L or $10^{-9}$ mol/1,
   adding to said reaction volume in a second step a second ligand able to bind specifically to said first ligand with a dissociation constant equal or below $10^{-6}$ mol/L, $10^{-7}$ mol/L, $10^{-8}$ mol/L or $10^{-9}$ mol/L, wherein said second ligand comprises a first polypeptide,
   adding to said reaction volume in a third step a precursor polypeptide, wherein said precursor polypeptide is cleavable by said first polypeptide into a second polypeptide, and a peptide substrate of said second polypeptide comprising a luminescent first FRET partner and a second FRET partner, wherein said first FRET partner and said second FRET partner are able to interact in such a way that the luminescent signal of said first FRET partner is changed with spatial approximation of said first FRET partner and said second FRET partner, and wherein said substrate is cleavable by said second polypeptide between said first FRET partner and said second FRET partner, quantifying the amount of said analyte by measurement of the luminescence of said first FRET partner or said second FRET partner, wherein said precursor polypeptide is a polypeptide according to claim 1.

10. The method according to claim 9, wherein said substrate is or comprises a peptide which has an amino acid sequence selected from SEQ ID NO 06, SEQ ID NO 07, SEQ ID NO 08, SEQ ID NO 09, SEQ ID NO 10, SEQ ID NO 11, SEQ ID NO 12, SEQ ID NO 13, SEQ ID NO 14, SEQ ID NO 15, SEQ ID NO 16 and SEQ ID NO 17.

11. The method according to claim 9 or 10, wherein said first polypeptide having a proteolytic activity is or comprises the human enteropeptidase catalytic light chain or a polypeptide characterized by SEQ ID NO 05.

12. The method according to claim 9, wherein said first FRET partner is selected from fluorescein and H.

13. The method according to claim 9, wherein said second FRET partner is selected from Atto612Q, Cy5, TAMRA, BHQ-0, BHQ-1, BHQ-2, BHQ-3 BHQ-10, Dabysyl, QXL 490, QXL 570, QXL 610, QXL 670, QXL 680, Iowa black FQ, Iowa black RQ, IRDye QC-1 and Eclipse Dark Quencher.

14. A host cell comprising a nucleic acid sequence according to claim 6.

* * * * *

SEQUENCE LISTING

<160> NUMBER OF SEQ ID NOS: 18

<210> SEQ ID NO 1
<211> LENGTH: 232
<212> TYPE: PRT
<213> ORGANISM: Artificial Sequence
<220> FEATURE:
<223> OTHER INFORMATION: PRSS1-sc, a supercharged variant of human
      trypsinogen-1

<400> SEQUENCE: 1

Met Gly Phe Asp Asp Asp Asp Lys Ile Val Gly Gly Tyr Asn Cys Ala
1               5                   10                  15

Ala His Ser Val Pro Tyr Gln Val Ser Leu Asn Ser Gly Tyr His Phe
            20                  25                  30

Cys Gly Gly Ser Leu Ile Asn Glu Gln Trp Val Val Ser Ala Gly His
        35                  40                  45

Cys Tyr Lys Ser Arg Ile Gln Val Arg Leu Gly Glu His Asn Ile Lys
    50                  55                  60

Val Leu Glu Gly Asn Glu Gln Phe Ile Asn Ala Ala Lys Ile Ile Arg
65                  70                  75                  80

His Pro Gln Tyr Asp Arg Lys Thr Leu Asn Asn Asp Ile Met Leu Ile
                85                  90                  95

Lys Leu Ser Ser Arg Ala Val Ile Asn Ala Lys Val Ser Thr Ile Ser
            100                 105                 110

Leu Pro Thr Ala Pro Pro Ala Thr Gly Thr Leu Cys Leu Ile Ser Gly
        115                 120                 125

Trp Gly Asn Thr Ala Ser Ser Gly Ala Lys Asn Pro Asp Leu Leu Gln
    130                 135                 140

Cys Leu Asn Ala Pro Val Leu Ser Gln Ala Lys Cys Glu Ala Ser Tyr
145                 150                 155                 160

Pro Gly Lys Ile Thr Ser Asn Met Phe Cys Val Gly Phe Leu Glu Gly
                165                 170                 175

Gly Lys Asp Ser Cys Gln Gly Asp Ser Gly Gly Pro Val Val Cys Asn
            180                 185                 190

Gly Gln Leu Gln Gly Val Val Ser Trp Gly Asp Gly Cys Ala Gln Lys
        195                 200                 205

Asn Lys Pro Gly Val Tyr Thr Lys Val Tyr Asn Tyr Val Lys Trp Ile
    210                 215                 220

Lys Asn Thr Ile Ala Ala Asn Ser
225                 230

<210> SEQ ID NO 2
<211> LENGTH: 699
<212> TYPE: DNA
<213> ORGANISM: Artificial Sequence
<220> FEATURE:
<223> OTHER INFORMATION: PRSS1-sc, DNA encoding a supercharged variant
      of human trypsinogen-1

<400> SEQUENCE: 2
atgggctttg atgatgatga caagatcgtt gggggctaca actgtgcggc gcattctgtc      60
ccctaccagg tgtccctgaa ttctggctac cacttctgtg gtggctccct catcaacgaa    120
cagtgggtgg tatcagcagg ccactgctac aagtcccgca tccaggtgag actgggagag    180
cacaacatca aagtcctgga ggggaatgag cagttcatca atgcagccaa gatcatccgc    240
cacccccaat acgacaggaa gactctgaac aatgacatca tgttaatcaa gctctcctca    300
cgtgcagtaa tcaacgccaa agtgtccacc atctctctgc ccaccgcccc tccagccact    360
ggcacgctgt gcctcatctc tggctggggc aacactgcga gctctggcgc caaaaaccca    420
gacctgctgc agtgcctgaa cgctcctgtg ctgagccagg ctaagtgtga agcctcctac    480
cctggaaaga ttaccagcaa catgttctgt gtgggcttcc ttgagggagg caaggattca    540

```
tgtcagggtg attctggtgg ccctgtggtc tgcaatggac agctccaagg agttgtctcc    600
tggggtgatg gctgtgccca gaagaacaag cctggagtct acaccaaggt ctacaactat    660
gtgaaatgga ttaagaacac catagctgcc aatagctaa                           699
```

```
<210> SEQ ID NO 3
<211> LENGTH: 232
<212> TYPE: PRT
<213> ORGANISM: Homo sapiens

<400> SEQUENCE: 3
```

```
Met Gly Phe Asp Asp Asp Lys Ile Val Gly Gly Tyr Asn Cys Glu
1               5                   10                  15

Glu Asn Ser Val Pro Tyr Gln Val Ser Leu Asn Ser Gly Tyr His Phe
            20                  25                  30

Cys Gly Gly Ser Leu Ile Asn Glu Gln Trp Val Val Ser Ala Gly His
            35                  40                  45

Cys Tyr Lys Ser Arg Ile Gln Val Arg Leu Gly Glu His Asn Ile Glu
    50                  55                  60

Val Leu Glu Gly Asn Glu Gln Phe Ile Asn Ala Ala Lys Ile Ile Arg
65                  70                  75                  80

His Pro Gln Tyr Asp Arg Lys Thr Leu Asn Asn Asp Ile Met Leu Ile
                85                  90                  95

Lys Leu Ser Ser Arg Ala Val Ile Asn Ala Arg Val Ser Thr Ile Ser
            100                 105                 110

Leu Pro Thr Ala Pro Pro Ala Thr Gly Thr Lys Cys Leu Ile Ser Gly
            115                 120                 125

Trp Gly Asn Thr Ala Ser Ser Gly Ala Asp Tyr Pro Asp Glu Leu Gln
    130                 135                 140

Cys Leu Asp Ala Pro Val Leu Ser Gln Ala Lys Cys Glu Ala Ser Tyr
145                 150                 155                 160

Pro Gly Lys Ile Thr Ser Asn Met Phe Cys Val Gly Phe Leu Glu Gly
                165                 170                 175

Gly Lys Asp Ser Cys Gln Gly Asp Ser Gly Gly Pro Val Val Cys Asn
            180                 185                 190

Gly Gln Leu Gln Gly Val Val Ser Trp Gly Asp Gly Cys Ala Gln Lys
            195                 200                 205

Asn Lys Pro Gly Val Tyr Thr Lys Val Tyr Asn Tyr Val Lys Trp Ile
    210                 215                 220

Lys Asn Thr Ile Ala Ala Asn Ser
225                 230
```

```
<210> SEQ ID NO 4
<211> LENGTH: 699
<212> TYPE: DNA
<213> ORGANISM: Homo sapiens

<400> SEQUENCE: 4
```

```
atgggctttg atgatgatga caagatcgtt ggggctaca actgtgagga gaattctgtc     60
ccctaccagg tgtccctgaa ttctggctac cacttctgtg gtggctccct catcaacgaa   120
cagtgggtgg tatcagcagg ccactgctac aagtcccgca tccaggtgag actgggagag   180
cacaacatcg aagtcctgga ggggaatgag cagttcatca atgcagccaa gatcatccgc   240
cacccccaat acgacaggaa gactctgaac aatgacatca tgttaatcaa gctctcctca   300
cgtgcagtaa tcaacgcccg cgtgtccacc atctctctgc ccaccgcccc tccagccact   360
```

-continued

```
ggcacgaagt gcctcatctc tggctggggc aacactgcga gctctggcgc cgactaccca    420
gacgagctgc agtgcctgga cgctcctgtg ctgagccagg ctaagtgtga agcctcctac    480
cctggaaaga ttaccagcaa catgttctgt gtgggcttcc ttgagggagg caaggattca    540
tgtcagggtg attctggtgg ccctgtggtc tgcaatggac agctccaagg agttgtctcc    600
tggggtgatg gctgtgccca gaagaacaag cctggagtct acaccaaggt ctacaactat    660
gtgaaatgga ttaagaacac catagctgcc aatagctaa                            699
```

<210> SEQ ID NO 5
<211> LENGTH: 235
<212> TYPE: PRT
<213> ORGANISM: Artificial Sequence
<220> FEATURE:
<223> OTHER INFORMATION: hEP1-sc-C112S, a supercharged variant of human enteropeptidase

<400> SEQUENCE: 5

```
Ile Val Gly Gly Ser Asp Ala Lys Glu Gly Ala Trp Pro Trp Val Val
1               5                   10                  15

Gly Leu Tyr Tyr Asp Asp Arg Leu Leu Cys Gly Ala Ser Leu Val Ser
            20                  25                  30

Ser Asp Trp Leu Val Ser Ala Ala His Cys Val Tyr Gly Arg Asn Leu
        35                  40                  45

Glu Pro Ser Lys Trp Thr Ala Ile Leu Gly Leu His Met Lys Ser Asn
    50                  55                  60

Leu Thr Ser Pro Gln Thr Val Pro Arg Leu Ile Asp Glu Ile Val Ile
65                  70                  75                  80

Asn Pro His Tyr Asn Arg Arg Lys Asp Asn Asp Ile Ala Met Met
                85                  90                  95

His Leu Glu Phe Lys Val Asn Tyr Thr Asp Tyr Ile Gln Pro Ile Ser
            100                 105                 110

Leu Pro Glu Glu Asn Gln Val Phe Pro Pro Gly Arg Asn Cys Ser Ile
        115                 120                 125

Ala Gly Trp Gly Thr Val Val Tyr Gln Gly Thr Thr Ala Asp Ile Leu
    130                 135                 140

Gln Glu Ala Asp Val Pro Leu Leu Ser Asn Glu Arg Cys Gln Gln Gln
145                 150                 155                 160

Met Pro Glu Tyr Asn Ile Thr Glu Asn Met Ile Cys Ala Gly Tyr Glu
                165                 170                 175

Glu Gly Gly Ile Asp Ser Cys Gln Gly Asp Ser Gly Gly Pro Leu Met
            180                 185                 190

Cys Gln Glu Asn Asn Arg Trp Phe Leu Ala Gly Val Thr Ser Phe Gly
        195                 200                 205

Tyr Glu Cys Ala Leu Pro Asn Arg Pro Gly Val Tyr Ala Arg Val Ser
    210                 215                 220

Arg Phe Thr Glu Trp Ile Gln Ser Phe Leu His
225                 230                 235
```

<210> SEQ ID NO 6
<211> LENGTH: 5
<212> TYPE: PRT
<213> ORGANISM: Artificial Sequence
<220> FEATURE:
<223> OTHER INFORMATION: peptide 3, a substrate of human trypsin-1

<400> SEQUENCE: 6

Gly Arg Ala Ser Cys
1               5

<210> SEQ ID NO 7
<211> LENGTH: 6
<212> TYPE: PRT
<213> ORGANISM: Artificial Sequence
<220> FEATURE:
<223> OTHER INFORMATION: peptide 4, a substrate of human trypsin-1

<400> SEQUENCE: 7

Gly Arg Ala Ser Thr Cys
1               5

<210> SEQ ID NO 8
<211> LENGTH: 7
<212> TYPE: PRT
<213> ORGANISM: Artificial Sequence
<220> FEATURE:
<223> OTHER INFORMATION: peptide 5, a substrate of human trypsin-1

<400> SEQUENCE: 8

Gly Arg Ala Ser Thr Ser Cys
1               5

<210> SEQ ID NO 9
<211> LENGTH: 3
<212> TYPE: PRT
<213> ORGANISM: Artificial Sequence
<220> FEATURE:
<223> OTHER INFORMATION: peptide 6, a substrate of human trypsin-1

<400> SEQUENCE: 9

Gly Arg Cys
1

<210> SEQ ID NO 10
<211> LENGTH: 4
<212> TYPE: PRT
<213> ORGANISM: Artificial Sequence
<220> FEATURE:
<223> OTHER INFORMATION: peptide 7, a substrate of human trypsin-1

<400> SEQUENCE: 10

Gly Ser Arg Cys
1

<210> SEQ ID NO 11
<211> LENGTH: 5
<212> TYPE: PRT
<213> ORGANISM: Artificial Sequence
<220> FEATURE:
<223> OTHER INFORMATION: peptide 8, a substrate of human trypsin-1

<400> SEQUENCE: 11

Gly Ser Arg Ala Cys
1               5

<210> SEQ ID NO 12
<211> LENGTH: 6
<212> TYPE: PRT
<213> ORGANISM: Artificial Sequence
<220> FEATURE:
<223> OTHER INFORMATION: peptide 9, a substrate of human trypsin-1

<400> SEQUENCE: 12

Gly Ser Arg Ala Ser Cys

```
<210> SEQ ID NO 13
<211> LENGTH: 7
<212> TYPE: PRT
<213> ORGANISM: Artificial Sequence
<220> FEATURE:
<223> OTHER INFORMATION: peptide 10, a substrate of human trypsin-1

<400> SEQUENCE: 13

Gly Ser Arg Ala Ser Thr Cys
1               5

<210> SEQ ID NO 14
<211> LENGTH: 11
<212> TYPE: PRT
<213> ORGANISM: Artificial Sequence
<220> FEATURE:
<223> OTHER INFORMATION: peptide 11, a substrate of human trypsin-1

<400> SEQUENCE: 14

Gly Ser Ala Thr Arg Ala Ser Thr Glu Lys Cys
1               5                   10

<210> SEQ ID NO 15
<211> LENGTH: 10
<212> TYPE: PRT
<213> ORGANISM: Artificial Sequence
<220> FEATURE:
<223> OTHER INFORMATION: peptide 12, a substrate of human trypsin-1

<400> SEQUENCE: 15

Gly Pro Ala Arg Leu Ala Ile Ser Glu Cys
1               5                   10

<210> SEQ ID NO 16
<211> LENGTH: 3
<212> TYPE: PRT
<213> ORGANISM: Artificial Sequence
<220> FEATURE:
<223> OTHER INFORMATION: peptide 13, a substrate of human trypsin-1

<400> SEQUENCE: 16

Gly Pro Arg
1

<210> SEQ ID NO 17
<211> LENGTH: 4
<212> TYPE: PRT
<213> ORGANISM: Artificial Sequence
<220> FEATURE:
<223> OTHER INFORMATION: peptide 14, a substrate of human trypsin-1

<400> SEQUENCE: 17

Ser Arg Ala Lys
1

<210> SEQ ID NO 18
<211> LENGTH: 5932
<212> TYPE: DNA
<213> ORGANISM: Artificial Sequence
<220> FEATURE:
<223> OTHER INFORMATION: pET28 vector encoding the supercharged variant
      of human trypsinogen-1

<400> SEQUENCE: 18
tggcgaatgg gacgcgccct gtagcggcgc attaagcgcg gcgggtgtgg tggttacgcg    60
```

```
cagcgtgacc gctacacttg ccagcgccct agcgcccgct cctttcgctt tcttcccttc    120
ctttctcgcc acgttcgccg gctttccccg tcaagctcta atcgggggc tccctttagg    180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa atcccttaa   1440 cgtgagtttt cgttccactg agcgtcagac cccgtagaaa agatcaaagg atcttcttga   1500 gatcctttt ttctgcgcgt aatctgctgc ttgcaaacaa aaaaccacc gctaccagcg   1560 gtggtttgtt tgccggatca gagctacca actcttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccggggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg cctttttgctc acatgttctt tcctgcgtta   2160 tccccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
```

```
ggtcatggct gcgccccgac acccgccaac acccgctgac gcgccctgac gggcttgtct     2460
gctcccggca tccgcttaca gacaagctgt gaccgtctcc gggagctgca tgtgtcagag     2520
gttttcaccg tcatcaccga aacgcgcgag gcagctgcgg taaagctcat cagcgtggtc     2580
gtgaagcgat tcacagatgt ctgcctgttc atccgcgtcc agctcgttga gtttctccag     2640
aagcgttaat gtctggcttc tgataaagcg ggccatgtta agggcggttt tttcctgttt     2700
ggtcactgat gcctccgtgt aagggggatt tctgttcatg ggggtaatga taccgatgaa     2760
acgagagagg atgctcacga tacgggttac tgatgatgaa catgcccggt tactggaacg     2820
ttgtgagggt aaacaactgg cggtatggat gcggcgggac cagagaaaaa tcactcaggg     2880
tcaatgccag cgcttcgtta atacagatgt aggtgttcca cagggtagcc agcagcatcc     2940
tgcgatgcag atccggaaca taatggtgca gggcgctgac ttccgcgttt ccagactttta     3000 cgaaacacgg aaaccgaaga ccattcatgt tgttgctcag tcgcagacg ttttgcagca     3060 gcagtcgctt cacgttcgct cgcgtatcgg tgattcattc tgctaaccag taaggcaacc     3120
ccgccagcct agccgggtcc tcaacgacag gagcacgatc atgcgcaccc gtggggccgc     3180
catgccggcg ataatggcct gcttctcgcc gaaacgtttg gtggcgggac cagtgacgaa     3240
ggcttgagcg agggcgtgca agattccgaa taccgcaagc gacaggccga tcatcgtcgc     3300
gctccagcga aagcggtcct cgccgaaaat gacccagagc gctgccggca cctgtcctac     3360
gagttgcatg ataaagaaga cagtcataag tgcggcgacg atagtcatgc cccgcgccca     3420
ccggaaggag ctgactgggt tgaaggctct caagggcatc ggtcgagatc ccggtgccta     3480
atgagtgagc taacttacat taattgcgtt gcgctcactg cccgctttcc agtcgggaaa     3540
cctgtcgtgc cagctgcatt aatgaatcgg ccaacgcgcg gggagaggcg gtttgcgtat     3600
tgggcgccag ggtggttttt cttttcacca gtgagacggg caacagctga ttgcccttca     3660
ccgcctggcc ctgagagagt tgcagcaagc ggtccacgct ggtttgcccc agcaggcgaa     3720
aatcctgttt gatggtggtt aacggcggga tataacatga gctgtcttcg gtatcgtcgt     3780
atcccactac cgagatatcc gcaccaacgc gcagcccgga ctcggtaatg gcgcgcattg     3840
cgcccagcgc catctgatcg ttggcaacca gcatcgcagt gggaacgatg ccctcattca     3900
gcatttgcat ggtttgttga aaaccggaca tggcactcca gtcgccttcc cgttccgcta     3960
tcggctgaat ttgattgcga gtgagatatt tatgccagcc agccagacgc agacgcgccg     4020
agacagaact taatgggccc gctaacagcg cgatttgctg gtgacccaat gcgaccagat     4080
gctccacgcc cagtcgcgta ccgtcttcat gggagaaaat aatactgttg atgggtgtct     4140
ggtcagagac atcaagaaat aacgccggaa cattagtgca ggcagcttcc acagcaatgg     4200
catcctggtc atccagcgga tagttaatga tcagcccact gacgcgttgc gcgagaagat     4260
tgtgcaccgc cgctttacag gcttcgacgc cgcttcgttc taccatcgac accaccacgc     4320
tggcacccag ttgatcggcg cgagatttaa tcgccgcgac aatttgcgac ggcgcgtgca     4380
gggccagact ggaggtggca acgccaatca gcaacgactg tttgcccgcc agttgttgtg     4440
ccacgcggtt gggaatgtaa ttcagctccg ccatcgccgc ttccacttttt tcccgcgttt     4500 tcgcagaaac gtggctggcc tggttcacca cgcgggaaac ggtctgataa gagacaccgg     4560
catactctgc gacatcgtat aacgttactg gtttcacatt caccaccctg aattgactct     4620
cttccgggcg ctatcatgcc ataccgcgaa aggttttgcg ccattcgatg gtgtccggga     4680
tctcgacgct ctcccttatg cgactcctgc attaggaagc agcccagtag taggttgagg     4740
ccgttgagca ccgccgccgc aaggaatggt gcatgcaagg agatggcgcc caacagtccc     4800
```

```
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggctttg atgatgatga caagatcgtt    5100
gggggctaca actgtgcggc gcattctgtc ccctaccagg tgtccctgaa ttctggctac    5160
cacttctgtg gtggctccct catcaacgaa cagtgggtgg tatcagcagg ccactgctac    5220
aagtcccgca tccaggtgag actgggagag cacaacatca aagtcctgga ggggaatgag    5280
cagttcatca atgcagccaa gatcatccgc cacccccaat acgacaggaa gactctgaac    5340
aatgacatca tgttaatcaa gctctcctca cgtgcagtaa tcaacgccaa agtgtccacc    5400
atctctctgc ccaccgcccc tccagccact ggcacgctgt gcctcatctc tggctggggc    5460
aacactgcga gctctggcgc caaaaaccca gacctgctgc agtgcctgaa cgctcctgtg    5520
ctgagccagg ctaagtgtga agcctcctac cctggaaaga ttaccagcaa catgttctgt    5580
gtgggcttcc ttgagggagg caaggattca tgtcagggtg attctggtgg ccctgtggtc    5640
tgcaatggac agctccaagg agttgtctcc tggggtgatg gctgtgccca gaagaacaag    5700
cctggagtct acaccaaggt ctacaactat gtgaaatgga ttaagaacac catagctgcc    5760
aatagctaac tcgagcacca ccaccaccac cactgagatc cggctgctaa caaagcccga    5820
aaggaagctg agttggctgc tgccaccgct gagcaataac tagcataacc ccttggggcc    5880
tctaaacggg tcttgagggg ttttttgctg aaaggaggaa ctatatccgg at            5932
```